United States Patent
Ohki et al.

(10) Patent No.: US 6,810,872 B1
(45) Date of Patent: Nov. 2, 2004

(54) INHALANT MEDICATOR

(75) Inventors: Hisatomo Ohki, Gunma (JP); Shigemi Nakamura, Gunma (JP); Kazunori Ishizeki, Gunma (JP); Yoshiyuki Yazawa, Gunma (JP); Akira Yanagawa, Yokohama (JP)

(73) Assignees: Unisia Jecs Corporation, Atsugi (JP); Dott Limited Company, Yokohama (JP)

( * ) Notice: Subject to any disclaimer, the term of this patent is extended or adjusted under 35 U.S.C. 154(b) by 433 days.

(21) Appl. No.: 09/703,794

(22) Filed: Nov. 2, 2000

(30) Foreign Application Priority Data

Dec. 10, 1999 (JP) .......................................... 11-352280
Dec. 10, 1999 (JP) .......................................... 11-352281

(51) Int. Cl.[7] ......................... A61M 15/00; B65D 83/04
(52) U.S. Cl. .......................... 128/203.15; 128/203.21; 206/528; 206/532
(58) Field of Search ....................... 128/203.12, 203.15, 128/203.21, 205.21, 205.24; 604/58; 206/528, 222, 828, 469, 532, 538

(56) References Cited

U.S. PATENT DOCUMENTS

| | | | | |
|---|---|---|---|---|
| 3,967,761 A | * | 7/1976 | Melton et al. .............. | 222/635 |
| 4,089,415 A | * | 5/1978 | Laib ........................ | 206/484.2 |
| 4,298,125 A | * | 11/1981 | Berghahn et al. .......... | 206/531 |
| 4,778,054 A | * | 10/1988 | Newell et al. .............. | 206/531 |
| 5,239,991 A | | 8/1993 | Chawla et al. | |
| 5,349,947 A | * | 9/1994 | Newhouse et al. ..... | 128/203.21 |
| 5,366,122 A | | 11/1994 | Guentert et al. | |
| 5,533,502 A | | 7/1996 | Piper | |
| 5,575,281 A | * | 11/1996 | Mecikalski ............ | 128/203.21 |
| 5,622,166 A | * | 4/1997 | Eisele et al. ........... | 128/203.12 |
| 5,669,378 A | * | 9/1997 | Pera et al. ............. | 128/203.21 |
| 5,685,294 A | | 11/1997 | Gupte et al. | |
| 5,715,810 A | | 2/1998 | Armstrong et al. | |
| 5,881,719 A | * | 3/1999 | Gottenauer et al. .... | 128/203.15 |
| 6,098,619 A | * | 8/2000 | Britto et al. ........... | 128/203.15 |

FOREIGN PATENT DOCUMENTS

| | | |
|---|---|---|
| EP | 0 711 572 A1 | 5/1996 |
| GB | 2 129 691 A | 5/1984 |
| GB | 2 169 265 A | 7/1986 |
| GB | 2 178 965 A | 2/1987 |
| GB | 2 340 758 A | 3/2000 |
| JP | 59-088158 | 5/1984 |
| JP | 62-041668 | 2/1987 |
| WO | WO 99/07426 A1 | 2/1999 |
| WO | WO 99/47199 A1 | 9/1999 |

* cited by examiner

Primary Examiner—Henry Bennett
Assistant Examiner—Mital Patel
(74) Attorney, Agent, or Firm—Foley & Lardner LLP

(57) ABSTRACT

A blister pack for a inhalant medicator has a plurality of medical powder storage chambers spaced apart from each other in a circumferential direction. The inhalant medicator includes a pricking tool with a pair of parallel pins that prick inflow and outflow holes in one of the medical powder storage chambers during a preliminary operation of inhalant medication. The inflow and outflow holes are spaced apart from each other by a predetermined distance in a direction parallel to a lid panel of the blister pack to produce turbulent airflow within the medical powder storage chamber during inhalation during which the medical powder is inhaled by a patient's breathing. The medical powder storage chambers are dimensioned and designed to properly regulate or control properties of the airflow passing through the medical storage chamber, to ensure the airflow is suitable for the medical powder storage chamber.

17 Claims, 24 Drawing Sheets

INHALANT MEDICATOR

TECHNICAL FIELD

The present invention relates to an inhalant medicator suitable to prescribe granular or powdered medicines toward and within lungs of a patient by way of breathing action of the patient, and particularly to a blister pack suitable for the inhalant medicator.

BACKGROUND ART

Generally, there are two methods of prescribing medical powder toward and within lungs of an asthmatic patient, that is, one being a method by which a medicine is inhaled by way of a liquid aerosol atomizer, and the other being an inhalation treatment by way of which granular or powdered medicines (which will be hereinafter referred to as "medical powder") encapsulated in a capsule or stored in a medical powder storage chamber are inhaled.

Of these methods for an asthmatic patient, an inhalant medicator used for an inhalation treatment where a dose of medical powder is inhaled, is generally constructed of: (a) a medicator body including a capsule housing chamber (or a medical powder storage chamber) at one axial end and equipped at the other axial end with an inhalant port through which the medical powder is inhaled, (b) an air passageway communicating the inhalant port with the atmosphere via the capsule housing chamber, and (c) a pricking tool which is provided for pricking holes in the capsule accommodated in the capsule housing chamber.

In recent years, there have been proposed and developed various inhalant medicators utilizing a blister pack having a set of blisters (a plurality of blistered medical powder storage chambers) spaced apart from each other in the circumferential direction, for inhalant medication. Such inhalant medicators have been disclosed in Japanese Patent Provisional Publication Nos. 59-88158 and 62-41668.

The inhalant medicator as disclosed in the Japanese Patent Provisional Publication Nos. 59-88158 and 62-41668, includes a blister pack holder which holds a blister pack having a plurality of blisters circumferentially spaced apart from each other. The blister pack holder is rotatably mounted to a medicator body. Also, the blister pack installed on the holder consists of a base panel formed with a large number of blistered portions, a lid panel affixed onto the principal surface of the base panel and defining a plurality of medical powder storage chambers by hermetically covering the blistered portions of the base panel. A dose of medical powder is stored in each of the medical powder storage chambers.

In order to prescribe or administer the medical powder toward and within lungs of a patient by way of breathing action, first, the blister pack is installed on the pack holder of the inhalant medicator. Second, holes needed to intercommunicate the atmospheric side and the inhalant port via the internal space of the medical powder storage chamber are pricked by means of a single plunger having a needle-shaped pricking tip.

Under these conditions, when the patient draws his or her breath while taking the inhalant port in his or her mouth, air flow directed from the pricked holes through the medical powder storage chamber into the inhalant port enables medical powder stored in the medical powder storage chamber to be carried into the inhalant port. In this manner, medical powder stored in the storage chamber can be inhaled through the inhalant port into lungs of the patient.

In order to continuously perform inhalant medication, the blister pack is rotated by a predetermined angle together with the blister pack holder, and then the next medical powder storage chamber of the same blister pack is set at the pricking position. Thereafter, in the same manner described previously, a series of inhalant medication procedures are made. Thus, it is possible to consecutively dose a patient with a specified amount of medical powder by rotation of the blister pack holder without exchanging a capsule.

However, in the inhalant medicators as disclosed in the Japanese Patent Provisional Publication Nos. 59-88158 and 62-41668, in order to prick holes in the medical powder storage chamber of the blister pack, a single needle-shaped plunger is used as the pricking tool. Thus, two holes, penetrating the medical powder storage chamber aligned to each other in a direction perpendicular to upper and lower surfaces of the blister pack, are pricked or pierced in one blistered portion of the blister pack. Air introduced into the medical powder storage chamber (the blistered portion) flows straight through the medical powder storage chamber from one (the inflow side) of the two pricked holes to the other (the outflow side). Actually, various sorts of medical powder having different characteristics or properties, such as a condensation property, a particle size (fine powder, granule, or the like) are used.

SUMMARY OF THE INVENTION

In the previously-described inhalant medicator with a single needle-shaped plunger, it is impossible to adequately diffuse medical powder in a medical powder storage chamber of a blister pack by way of such straight air flow (directed from one pricked hole to the other) in which there is less turbulence and thus the air stream direction is almost same, and which has a substantially constant flow velocity. Thus, some medical powder may be undesirably left in the medical powder storage chamber after prescribing the medical powder toward within lungs of a patient by breathing action. As a result of this, the patient cannot inhale a specified amount of medical powder into the lungs, thus lowering medical benefits of powdered or granular medicines.

Accordingly, it is an object of the invention to provide an inhalant medicator, which avoids the aforementioned disadvantages.

It is another object of the invention to provide an inhalant medicator, which is capable of prescribing a specified amount of medical powder toward within lungs of a patient, while satisfactorily diffusing the medical powder stored in a medical powder storage chamber of a blister pack.

It is a still further object of the invention to provide a blister pack suitable for an inhalant medicator, which enhances a medication efficiency, effectively diffusing medical powder stored in a medical powder storage chamber of the blister pack depending on characteristics or properties of the medical powder, such as a strong condensation property, and a particle size.

In order to accomplish the aforementioned and other objects of the present invention, an inhalant medicator comprises a medicator body including a holder mounting portion at one axial end and an inhalant port at the other axial end for inhalation of medical powder, a holder detachably rotatably mounted to the holder mounting portion and holding thereon a blister pack having a plurality of medical powder storage chambers spaced apart from each other in a circumferential direction thereof, the medicator body having a portion defining an inflow air passage to supply atmosphere toward one of the plurality of medical powder storage chambers of the blister pack held on the holder which is mounted to the holder mounting portion, the medicator body having a portion defining an outflow air passage to flow out the medical powder stored in the one medical powder storage chamber of the blister pack held on the holder toward the inhalant port, and a pricking tool attached to the medicator body to prick an inflow hole and an outflow hole in the one medical powder storage chamber of the blister pack, so that the inflow hole is fluidly communicated with the inflow air passageway and the outflow hole is fluidly communicated with the outflow air passageway. The inflow and outflow holes are spaced apart from each other by a predetermined distance between a downstream end of the inflow air passageway and an upstream end of the outflow air passageway. It is preferable that the medicator body may comprise upper and lower medicator-body portions and a joining portion through which the upper and lower medicator-body portions are formed integral with each other, the upper and lower medicator-body portions defining therebetween a holder mounting groove which opens to three directions, and the holder comprising a disc-shaped holder so that the disc-shaped holder is inserted into and removed from within the holder mounting groove. More preferably, the medicator body has a protruded portion formed on the lower medicator-body portion which is a center of rotation of the holder, and the holder has a plurality of recessed fit portions each of which is formed on an upside of the holder and is fitted to one of the plurality of medical powder storage chambers of the blister pack, and the holder has a portion defining a guide groove which is formed on an underside of the holder to guide the protruded portion to the center of rotation of the holder. It is preferable that the inhalant medicator may further comprise a positioning mechanism provided between the holder mounting portion of the medicator body and the holder, for positioning the one medical powder storage chamber of the blister pack held on the holder at a predetermined pricking position of the pricking tool. More preferably, the positioning mechanism comprises a spring-loaded ball housed in a bore formed in the medicator body and closed at one end, and a spring operably disposed in the bore so as to bias the ball in a direction that causes a part of a spherical surface of the ball to be protruded through an opening end of the bore into the holder mounting groove.

According to another aspect of the invention, an inhalant medicator comprises a medicator body including a holder mounting portion at one axial end and an inhalant port at the other axial end for inhalation of medical powder, a holder detachably rotatably mounted to the holder mounting portion and holding thereon a blister pack having a plurality of blistered portions spaced apart from each other in a circumferential direction thereof, the medicator body having a portion defining a pair of inflow air passages to supply atmosphere toward one of the plurality of blistered portions of the blister pack held on the holder which is mounted to the holder mounting portion, the medicator body having a portion defining a pair of outflow air passages to flow out the medical powder stored in the one blistered portion of the blister pack held on the holder toward the inhalant port, a pricking tool attached to the medicator body and having a pair of pins to prick upper and lower inflow holes and upper and lower outflow holes in the one blistered portion of the blister pack, so that the upper inflow hole is fluidly communicated with a first one of the inflow air passageways, the lower inflow hole is fluidly communicated with the second inflow air passageway, the upper outflow hole is fluidly communicated with a first one of the outflow air passageways, the lower outflow hole is fluidly communicated with the second outflow air passageway, the upper inflow and outflow holes being spaced apart from each other by a predetermined distance between a downstream end of the first inflow air passageway and an upstream end of the first outflow air passageway, and the lower inflow and outflow holes being spaced apart from each other by a predetermined distance between a downstream end of the second inflow air passageway and an upstream end of the second outflow air passageway.

According to a further aspect of the invention, an inhalant medicator comprises a medicator body including a holder mounting portion at one axial end and an inhalant port at the other axial end for inhalation of medical powder, a holder detachably rotatably mounted to the holder mounting portion and holding thereon a blister pack having a plurality of medical powder storage chambers spaced apart from each other in a circumferential direction thereof, the medicator body having a portion defining an inflow air passage to supply atmosphere toward one of the plurality of medical powder storage chambers of the blister pack held on the holder which is mounted to the holder mounting portion, the medicator body having a portion defining an outflow air passage to flow out the medical powder stored in the one medical powder storage chamber of the blister pack held on the holder toward the inhalant port, a pricking means attached to the medicator body for pricking an inflow hole and an outflow hole in the one medical powder storage chamber of the blister pack during a preliminary operation of inhalant medication, so that the inflow hole is fluidly communicated with the inflow air passageway and the outflow hole is fluidly communicated with the outflow air passageway, and the pricking means comprising a pair of parallel pins spaced apart from each other by a predetermined distance smaller than a longitudinal length of each of the medical powder storage chambers of the blister pack, and the inflow and outflow holes are spaced apart from each other by the predetermined distance to produce turbulent air flow within the one medical powder storage chambers of the blister pack during the inhalant medication in which the medical powder is inhaled.

According to a still further aspect of the invention, a blister pack for an inhalant medicator comprises a base panel having a blistered portion, a lid panel affixed onto an obverse of the base panel to define a medical powder storage chamber by hermetically covering the blistered portion of the base panel, the blistered portion comprising a pair of substantially hemispherical convex portions in which inflow and outflow holes are pricked during a preliminary operation of inhalant medication, and a flow-constriction portion formed between the substantially hemispherical convex portions to define a flow-constriction orifice passage. It is preferable that the blister pack may further comprise flap valve disposed in the flow-constriction orifice passage.

According to another aspect of the invention, a blister pack for an inhalant medicator comprises a base panel having a blistered portion, a lid panel affixed onto an obverse of the base panel to define a medical powder storage chamber by hermetically covering the blistered portion of the base panel, the blistered portion comprising a pair of shallow pricked portions in which inflow and outflow holes are pricked during a preliminary operation of inhalant medication; and a medical powder collecting portion deeply recessed between the shallow pricked portions to pre-store medical powder therein.

According to another aspect of the invention, a blister pack for an inhalant medicator comprises a base panel having a blistered portion in which inflow and outflow holes are pricked during a preliminary operation of inhalant medication, a lid panel affixed onto an obverse of the base panel to define a medical powder storage chamber by hermetically covering the blistered portion of the base panel, and the blistered portion comprising a sloped surface which defines a shallow portion at a side of the inflow hole and defines a deep portion at a side of the outflow hole.

According to another aspect of the invention, a blister pack for an inhalant medicator comprises a base panel having a blistered portion in which inflow and outflow holes are pricked during a preliminary operation of inhalant medication, a lid panel affixed onto an obverse of the base panel to define a medical powder storage chamber by hermetically covering the blistered portion of the base panel, and the blistered portion comprising a sloped surface which defines a shallow portion at a side of the outflow hole and defines a deep portion at a side of the inflow hole.

The other objects and features of this invention will become understood from the following description with reference to the accompanying drawings.

DESCRIPTION OF THE PREFERRED EMBODIMENTS

Figure 1:
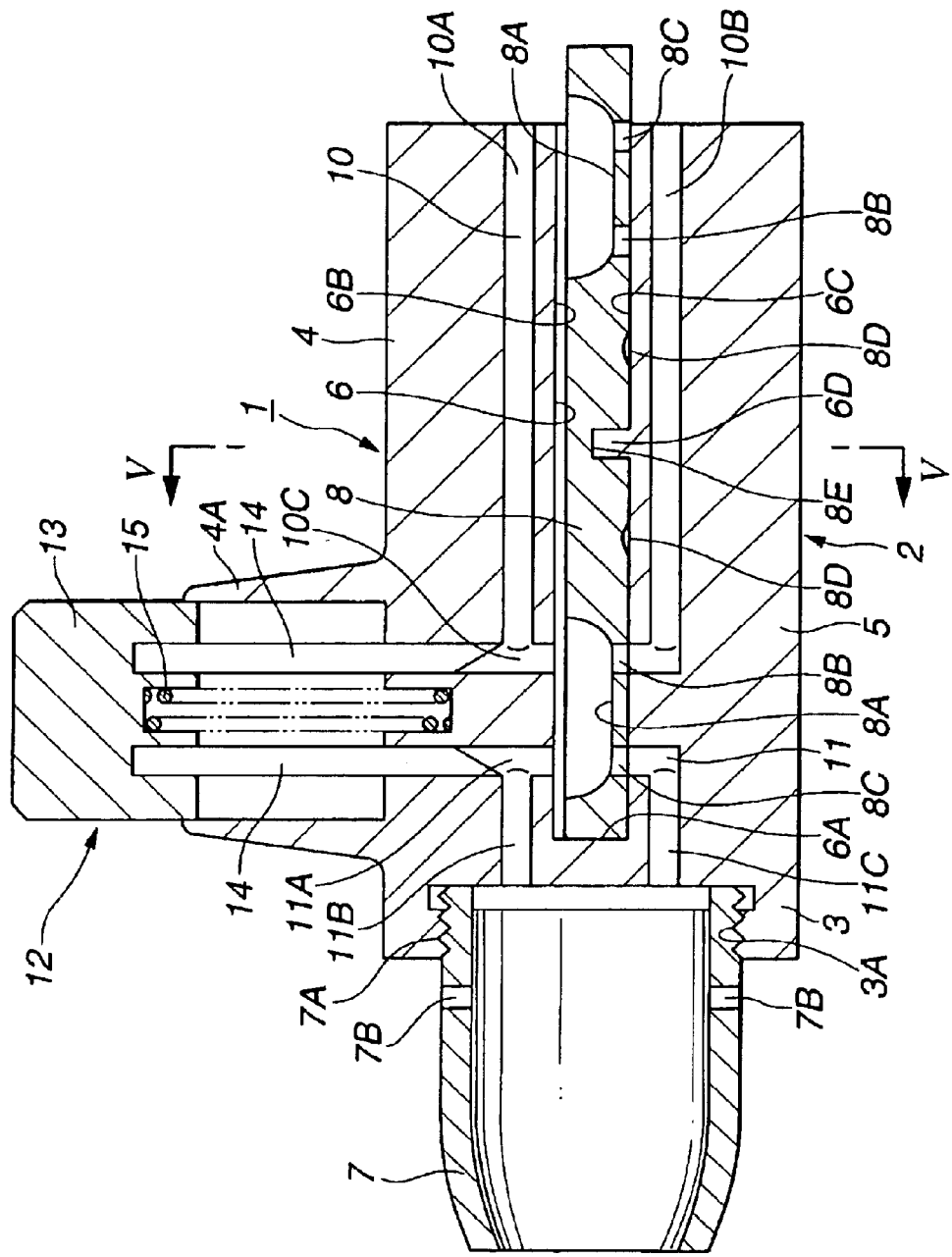
FIG. 1 is a longitudinal cross-sectional view illustrating one embodiment of an inhalant medicator of the invention.
Figure 2:
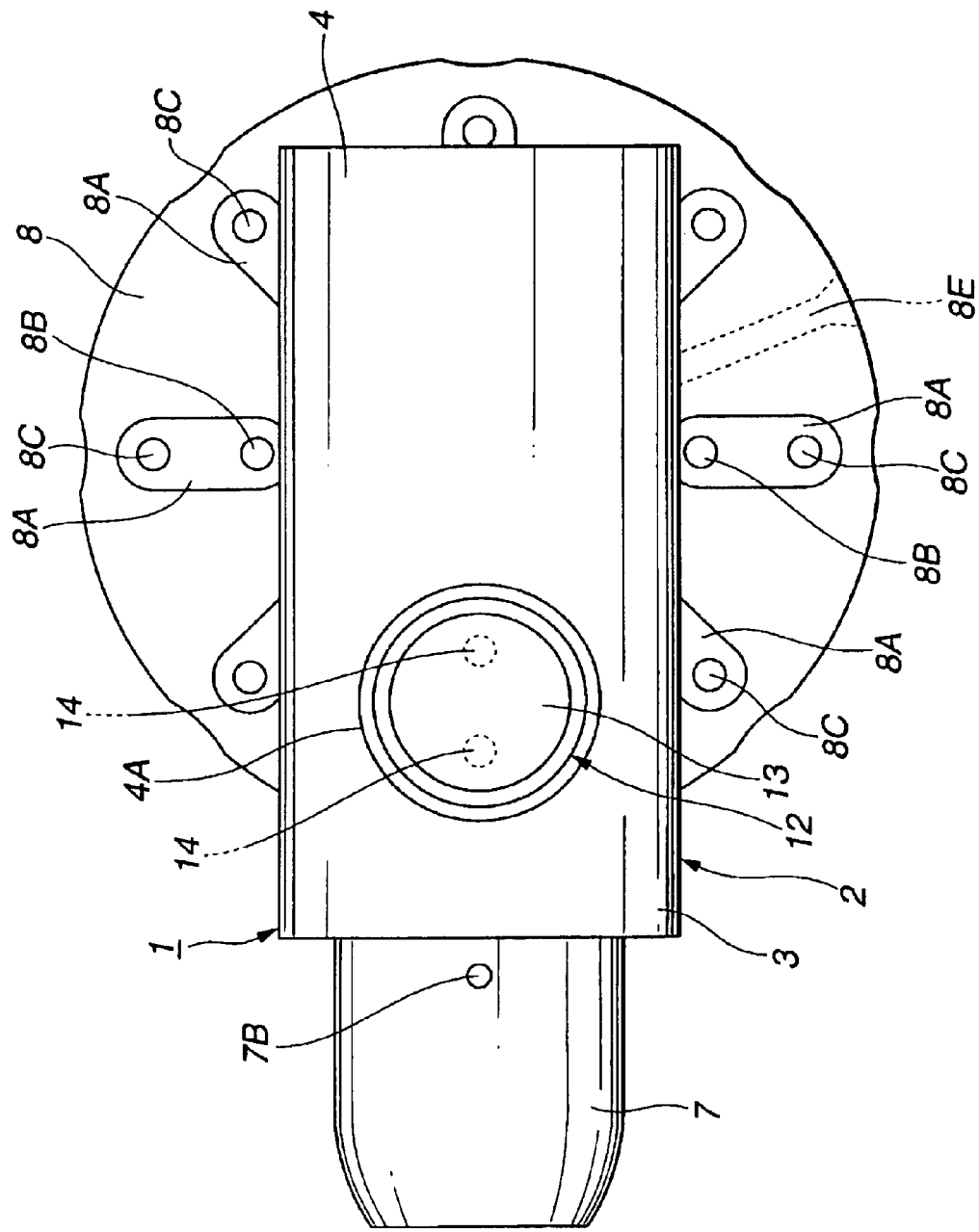
FIG. 2 is a plan view illustrating the inhalant medicator of the embodiment shown in FIG. 1.

Referring now to the drawings, particularly to FIGS. 1 through 11, there are shown the inhalant medicator of the first embodiment and a blister pack 16 applied to the inhalant medicator of the first embodiment. In FIGS. 1, 2, 9 and 10, reference sign 1 denotes an inhalant medicator assembly. The inhalant medicator assembly I is mainly constructed by a medicator body 2 and an inhalant port 7. As described later, the medicator body 2 is formed therein with a plurality of air passageways, and also serves as a blister pack holder mounting portion for a blister pack 16 which will be fully described later.

Figure 3:
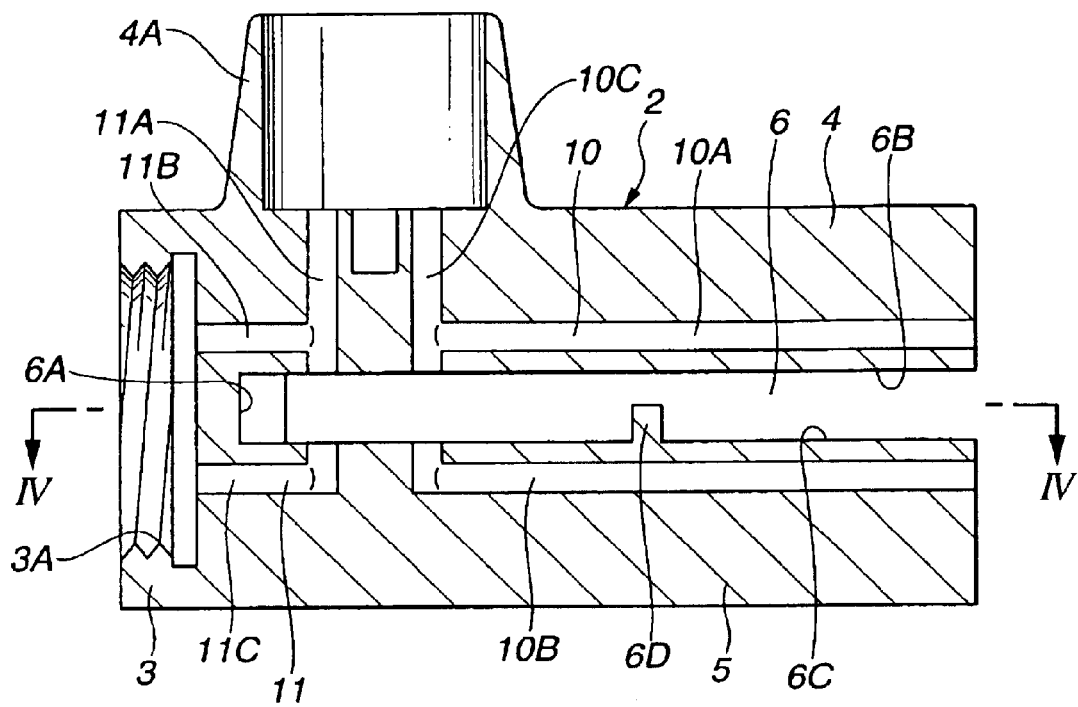
FIG. 3 is a longitudinal cross-sectional view illustrating details of a medicator body of the inhalant medicator shown in FIG. 1.
Figure 4:
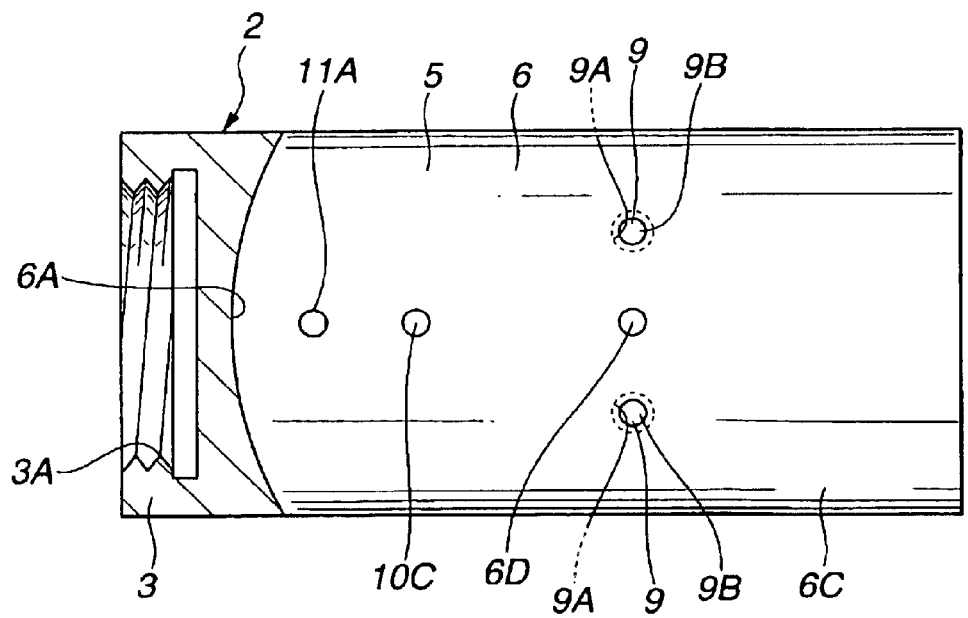
FIG. 4 is a longitudinal cross-sectional view of the medicator body, taken along the line IV-IV shown in FIG. 3.
Figure 5:
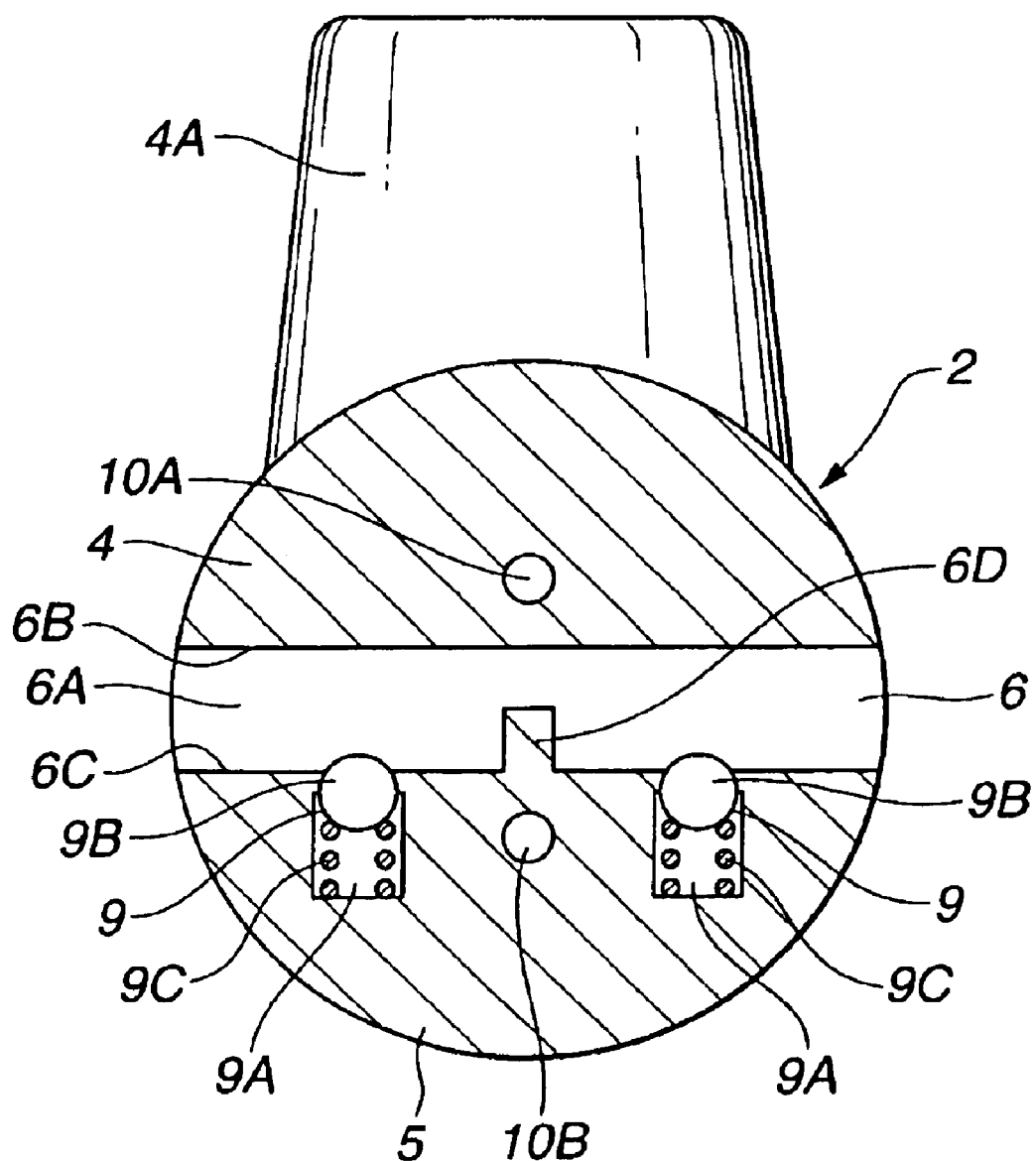
FIG. 5 is a lateral cross-sectional view illustrating the medicator body and a positioning mechanism, taken along the line V-V of FIG. 1.

As best seen in FIGS. 3 through 5, as a whole, the medicator body 2 is substantially cylindrical in shape. To be exact, the medicator body 2 is comprised of an upper medicator-body portion 4 having a substantially semi-circular cross section, a lower medicator-body portion 5 having a substantially semi-circular cross section (see FIGS. 3 and 5), and a substantially cylindrical joining portion 3 through which the upper and lower medicator-body portions 4 and 5 are formed integral with each other. Joining portion 3 has an internal thread portion 3A into which an external thread portion 7A of the inhalant port 7 is screwed.

Upper and lower medicator-body portions 4 and 5, each having the substantially semicircular cross section, are constructed in such a manner as to axially extend from the joining portion 3, so that their opposed flat surfaces, namely a ceiling wall surface 6B of a holder mounting groove 6 (described later) and a bottom surface 6C of the holder mounting groove 6, are parallel to each other and spaced apart from each other by a predetermined aperture (see FIGS. 3 and 5).

Medicator body 2 is also formed with the blister pack holder mounting groove 6 defined between upper and lower medicator-body portions 4 and 5. As a whole, the medicator body 2 is substantially cylindrical in shape. As clearly shown in FIGS. 1, 3 and 5, the upper medicator-body portion 4 is formed with a pricking tool guide 4A capable of slidably supporting or guiding a support portion 13 of a pricking tool (pricking means) 12 (described later). The holder mounting groove 6 is defined between upper and lower medicator-body portions 4 and 5 by three surfaces, namely an innermost end surface 6A forming part of the joining portion 3, the ceiling wall surface 6B corresponding to the underside of upper medicator-body portion 4, and the bottom surface 6C corresponding to the upside of lower medicator-body portion 5.

As viewed from the axial direction of the inhalant port 7, the holder mounting groove 6 opens to three directions, that is, leftwards and rightwards, and in one axial direction of the medicator body. The innermost end surface 6A of the groove 6 is formed into a concave circular-arc shape that fits the contour of the outer periphery of a blister pack holder 8 (see FIG. 4). The predetermined aperture defined between the ceiling wall surface 6B and the bottom surface 6C is dimensioned to be somewhat greater than the thickness dimension of the holder 8 (see FIG. 1).

The lower medicator-body portion 5 is formed with a protruded portion 6D extending upwards from a substantially central portion of the bottom surface 6C of holder mounting groove 6, such that the axis of the protruded portion 6D is perpendicular to the bottom surface 6C. The protruded portion 6D functions as a center of rotation (or an axis of rotation) of the blister pack holder 8. The protruded portion 6D is engaged with a guide groove 8E formed in the holder 8, when mounting the holder 8 into the groove 6. Inhalant port 7 is screwed into the other axial end of medicator body 2, and is substantially cylindrical hollow in shape. The top end (the left-hand side axial end of the inhalant medicator assembly 1 shown in FIG. 1) of inhalant port 7 is configured in a manner so as to gradually become diametrically larger along the axis moving toward the right side of FIG. 1.

As shown in FIG. 1, the root portion of inhalant port 7 is formed nearby the external thread portion 7A with a plurality of radially-extending auxiliary air passageways 7B, 7B, . . . (only two auxiliary air passageways 7B and 7B are shown in FIG. 1, for the purpose of illustrative simplicity). Each of the auxiliary air passageways 7B serves to avoid difficulty in breathing action by increasing a quantity of air flowing through the inhalant medicator during the breathing action. As can be appreciated from the cross section shown in FIG. 1, the inhalant port 7 is installed on the other axial end of the medicator body by screwing the external thread portion 7A of inhalant port 7 into the internal thread portion 3A of joining portion 3 of the medicator body.

On the other hand, the blister pack holder 8 is detachably rotatably mounted into the groove 6 of medicator body 2, so that the disc-shaped holder 8 is easily inserted into and removed from within the groove 6. When the innermost end of the guide groove 8E of the holder engages with the protruded portion 6D of the medicator body, the holder 8 is rotatable about the protruded portion 6D.

Figure 6:
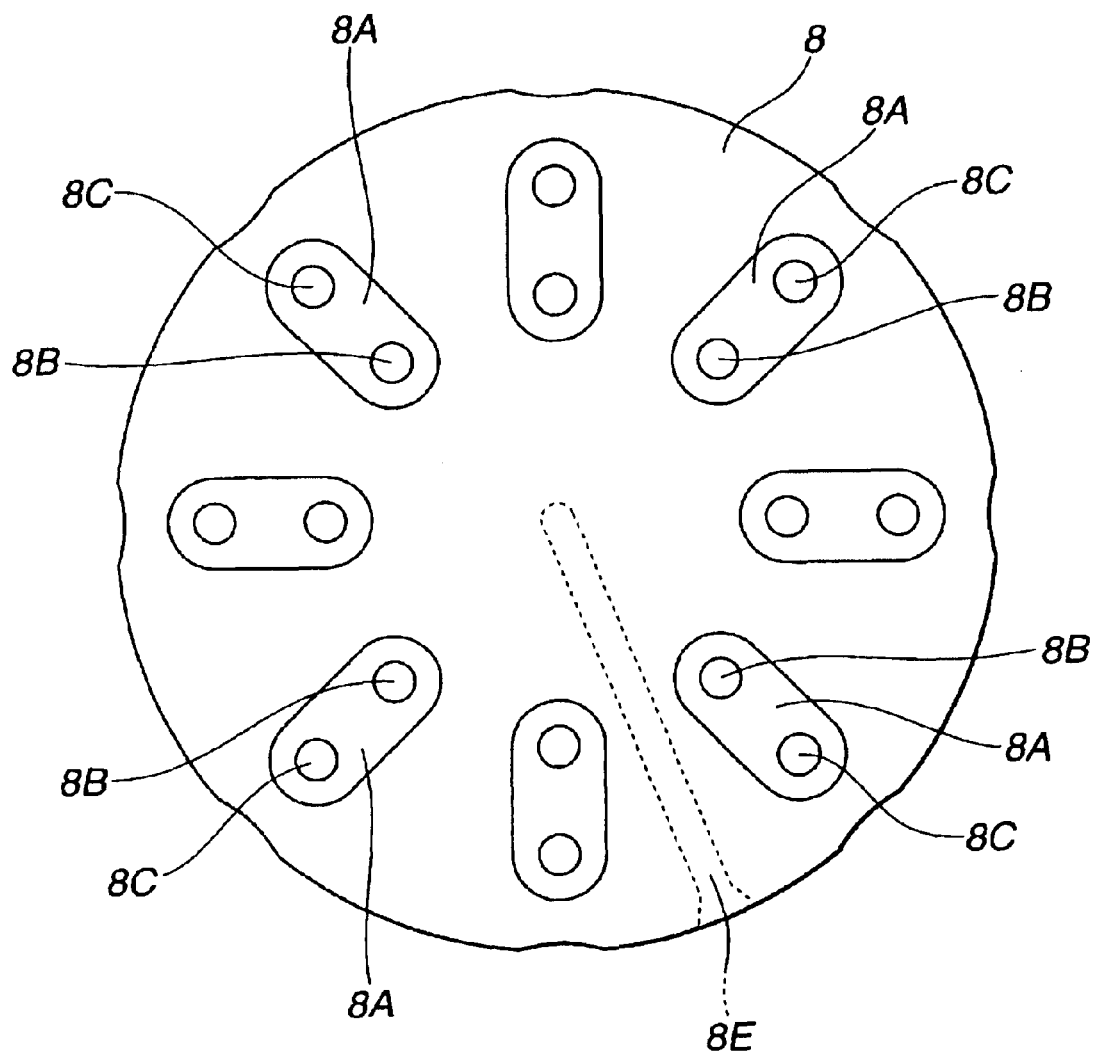
FIG. 6 is a top view illustrating a blister pack holder (8) mounted on the medicator body of the inhalant medicator shown in FIG. 1.
Figure 7:
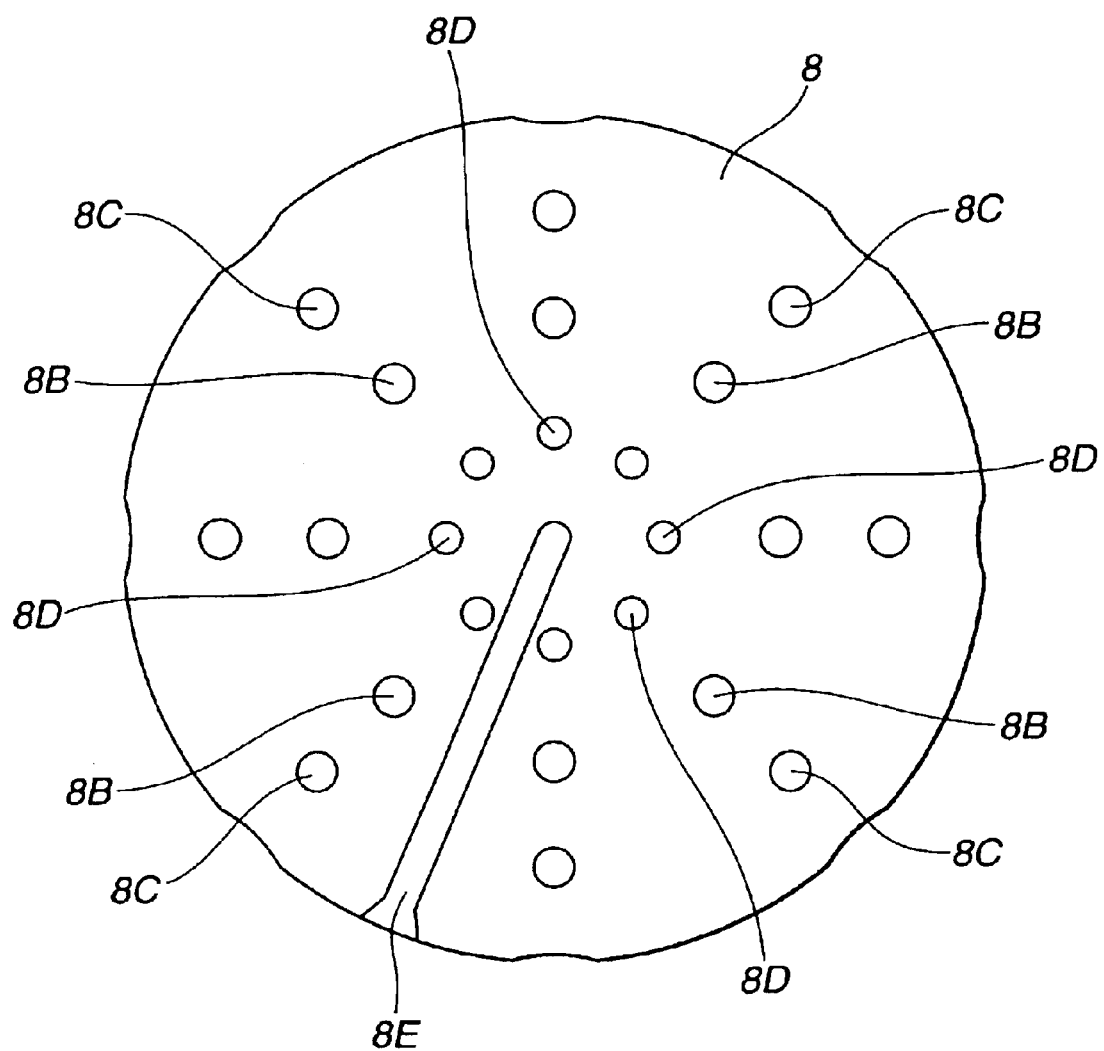
FIG. 7 is a bottom view illustrating the blister pack holder (8) shown in FIG. 6.

As clearly shown in FIGS. 6 and 7, the holder 8 has a substantially disc shape. As can be seen from the top view shown in FIG. 6, the holder 8 is formed on its upside with eight recessed fit portions 8A, 8A, . . . , 8A circumferentially spaced apart from each other by 45 degrees and located near its circumference. In the inhalant medicator of the first embodiment, the eight recessed fit portions 8A are configured or formed as eight radially-elongated, substantially semi-cylindrical cavities. Eight blistered portions 16B of blister pack 16 (described later) are integrally fitted into the respective eight recessed fit portions 8A of holder 8.

The holder 8 is formed in each of recessed fit portions 8A with an inflow pin insertion hole (a radially inward pin insertion hole) 8B and an outflow pin insertion hole (a radially-outward pin insertion hole) 8C spaced apart from each other in the radial direction of the holder 8 (viewing FIG. 6), so that two pin insertion holes 8B and 8C penetrate the disc-shaped holder 8 in a direction perpendicular to upper and lower surfaces of the holder 8. As viewed from the top view of FIG. 6 and from the bottom view of FIG. 8, and as can be appreciated from the circumferentially-spaced layout of eight radially-elongated recessed fit portions 8A, eight pairs of radially-aligned inward and outward pin insertion holes (8B, 8C) are also circumferentially spaced apart from each other by 45 degrees. As viewed from the bottom view shown in FIG. 7, the holder 8 is also formed with eight recessed fit portions 8D, 8D, . . . , 8D. The recessed fit portions 8D are formed as eight small spherical bowl cavities. In the shown embodiment, the number of the recessed fit portions 8D is an even number, for easy but reliable engagement between one diametrically-opposed pair (8D, 8D) of the eight recessed fit portions and a pair of spring-loaded balls (9A, 9A) of a positioning mechanism 9 (described later).

As fully described later, a positioning mechanism (positioning means) 9 is provided between the holder 8 and the blister pack holder mounting portion of the medicator body for positioning one of the medical powder storage chambers of the blister pack installed or held on the holder 8 at a predetermined pricking position. A pair of spherical ball portions (9B, 9B) included in the positioning mechanism 9 are easily fitted to one diametrically-opposed pair (8D, 8D) of the eight recessed fit portions. Such easy fit between two spherical ball portions (9B, 9B) and diametrically-opposed recessed portions (8D, 8D) ensures easy rotation of the holder 8 about the protruded portion 6D (serving as the axis of rotation of the holder 8) and is produced by proper mechanical snap action during rotary motion of the holder. In the shown embodiment, two spherical ball portions (9B, 9B) are comprised of spring-loaded balls included in the positioning mechanism 9 (described later).

The eight recessed fit portions 8D (eight small spherical bowl cavities) are located around the center of the holder 8. Each of recessed fit portions 8D is located on a straight line including two centers of the associated radially-aligned inward and outward pin insertion holes 8B and 8C. The eight recessed fit portions 8D are also circumferentially spaced apart from each other by 45 degrees.

The holder 8 is also formed on the underside with the guide groove 8E radially extending from the center of rotation of the holder 8. The guide groove 8E is formed to guide the protruded portion 6D of the holder mounting groove 6 toward the center of rotation of the holder 8. The holder 8 is inserted or mounted into the holder mounting groove 6 in accordance with the following procedures. First, the guide groove 8E is engaged with the protruded portion 6D under a condition where the blister pack 16 is installed on and fitted to the upside of the holder 8. Thereafter, the holder 8 having the blister pack 16 installed thereon, is inserted into the holder mounting groove 6 of medicator body 2, until the innermost end of the guide groove 8E of the holder reaches the protruded portion 6D of the medicator body.

As best seen in FIGS. 4 and 5, a component part denoted by 9 is the positioning mechanism (or positioning means). The positioning mechanism 9 includes a pair of spring-loaded ball housing bores (9A, 9A) each closed at one end. The bores (9A, 9A) are point-symmetrical with respect to the protruded portion 6D and formed in the bottom surface 6C (lower medicator-body portion 5) of holder mounting groove 6.

The positioning mechanism 9 also includes two spring-loaded spherical balls (9B, 9B) housed in the respective ball housing bores (9A, 9A) in an unremovable fashion so that the inside diameter of the opening end of each spring-loaded ball housing bore 9A is slightly less than the inside diameter of the other portion of the bore 9A, and two coil springs (9C, 9C), each operably disposed in the ball housing bore 9A in a manner so as to permanently bias the associated ball 9B in a direction that causes a part of the spherical surface of the ball 9B to be slightly protruded from the bottom surface 6C through an opening end of the bore 9A into the groove 6 of medicator body 2. In the shown embodiment, the positioning mechanism 9 is comprised of a snap-action mechanism with a pair of spring-loaded balls (9B, 9B).

With the previously-noted arrangement of the positioning mechanism 9, when the holder 8 is rotated under a condition where the holder 8 has been mounted into the groove 6 of medicator body 2, the two spring-loaded balls (9B, 9B) can be brought into engagement with the respective recessed fit portions (8D, 8D) of the holder 8. By way of the engagement between the two spring-loaded balls (9B, 9B) and the recessed fit portions (8D, 8D) with the rotary motion of the holder 8, one of eight radially-elongated recessed fit portions 8A (that is, one of eight medical powder storage chambers 16D of blister pack 16) is efficiently reliably positioned in a predetermined pricking position of the pricking tool 12 (or in a set position for inhalant medication).

Reference sign 10 denotes an inflow air passageway through which the atmosphere (outside air) can be introduced into or directed toward within the recessed fit portion 8A of the holder 8. The inflow air passageway 10 includes an upper axially-extending air passage 10A which is bored or formed in the upper medicator-body portion 4, and whose one axial end opens at one axial end of the upper medicator-body portion 4 to the atmosphere. In a similar manner, the inflow air passageway 10 includes a lower axially-extending air passage 10B which is bored or formed in the lower medicator-body portion 5, and whose one axial end opens at one axial end of the lower medicator-body portion 5 to the atmosphere.

The inflow air passageway 10 also includes a radially-extending pin insertion hole 10C formed in the medicator body 2 so that the pin insertion hole 10C radially extends from the pricking tool guide 4A via the upper medicator-body portion 4 toward the lower medicator-body portion 5. The radially-extending pin insertion hole 10C is fluidly communicated with the other axial end of each of the upper and lower axially-extending air passages 10A and 10B. The pin insertion hole 10C is designed to communicate with the inflow pin insertion hole 8B of the holder 8, when one of eight recessed fit portions 8A of the holder 8 is positioned in the pricking position.

On the other hand, reference sign 11 denotes an outflow air passageway through which medical powder stored in the medical powder storage chamber 16D of the blister pack 16 flows into the inhalant port 7. The outflow air passageway 11 includes a pin insertion hole 11A, an upper outflow air passage 11B, and a lower outflow air passage 11C. The pin insertion hole 11A radially extends in parallel with the pin insertion hole 10C of the inflow air passageway 10. The upper outflow air passage 11B axially extends from the upper medicator-body portion 4 via the joining portion 3 toward the inhalant port 7. One axial end of the upper outflow air passage 11B is fluidly communicated with the pin insertion hole 11A, whereas the other axial end opens to the interior space of the inhalant port 7. In a similar manner, one axial end of the lower outflow air passage 11C is fluidly communicated with the pin insertion hole 11A, whereas the other axial end opens to the interior space of the inhalant port 7.

In FIG. 1, a component part denoted by reference sign 12 is the pricking tool used to prick holes in the blister pack 16. As shown in FIG. 1, the pricking tool 12 includes the support portion 13 whose outer periphery is slidably supported or guided by a cylindrical inner peripheral wall of the pricking tool guide 4A, and a pair of parallel pins (14, 14) whose root portions are fixedly connected to the support portion 13, and whose tips are inserted into the respective pin insertion holes 10C and 11A. The pair of parallel pins are spaced apart from each other by a predetermined distance smaller than a longitudinal length of each of the blistered portions of the blister pack. The pricking tool 12 also includes a return spring 15 operably disposed between the support portion 13 and the upper medicator-body portion 4 for permanently biasing the support portion 13 and the pins (14, 14) toward their initial positions.

When the pricking action is performed, a patient pushes the support portion 13 of pricking tool 12 into the pricking tool guide 4A against the bias of the spring 15, and thus the two pins (14, 14) are deeply inserted into the respective pin insertion holes 10C and 11A. Thus, the tips of pins (14, 14) penetrate the blister pack 16. As a result of this, two inflow holes or two inflow ports (H1, H1) and two outflow holes or two outflow ports (H2, H2) are pricked respectively in the blistered portion 16B of a base panel 16A and a lid panel 16C of blister pack 16 (see FIGS. 10 and 11), so that two inflow holes (H1, H1) and two outflow holes (H2, H2) are pricked in a perpendicular to the upper surface of the lid panel of the blister pack, and two inflow holes (H1, H1) and two outflow holes (H2, H2) are spaced apart from each other by a predetermined distance which corresponds to a distance between the downstream end of the inflow air passage and the upstream end of the outflow air passageway.

As detailed hereunder, eight blistered portions 16B of the base panel 16A define eight medical powder storage chambers 16D in conjunction with the lid panel 16C. After pricking, as soon as the pushing force applied to the support portion 13 is removed, the support portion 13 and the two pins (14, 14) are returned back to their initial positions.

Figure 8:
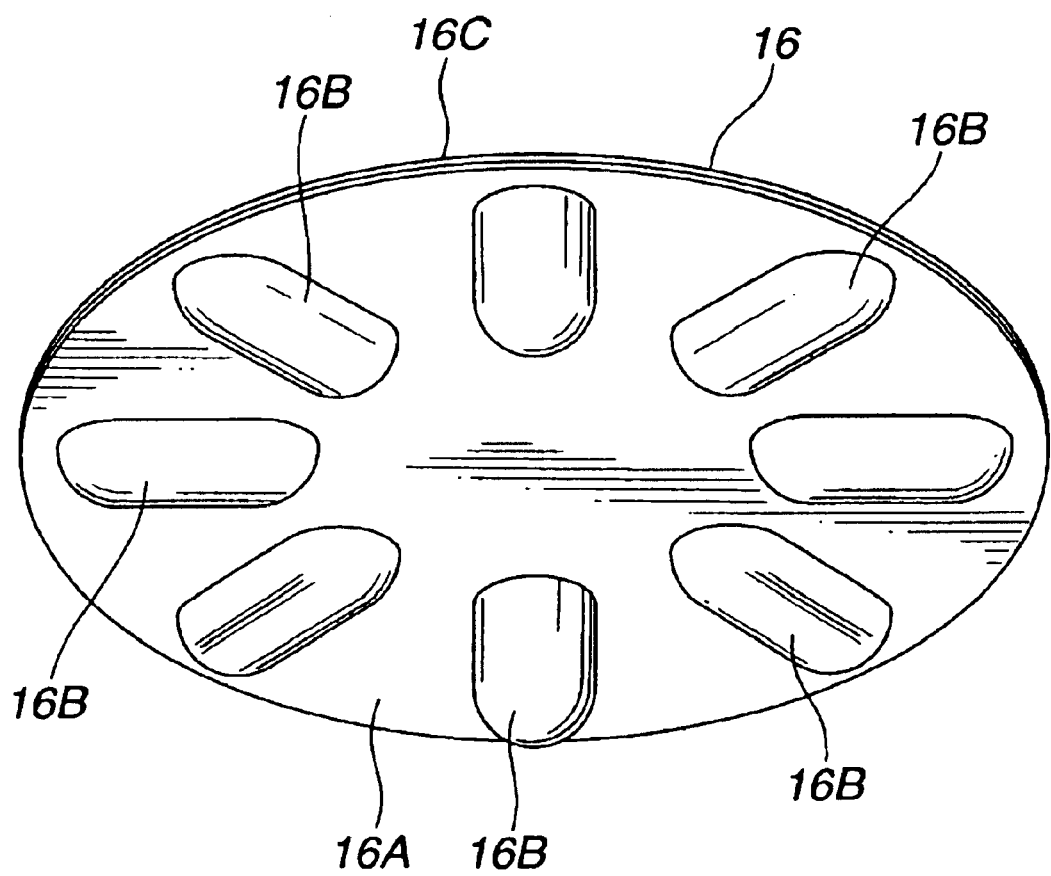
FIG. 8 is a perspective view of a blister pack (16) to be installed on the holder of FIG. 6, as viewed from its bottom side (its base panel side).
Figure 9:
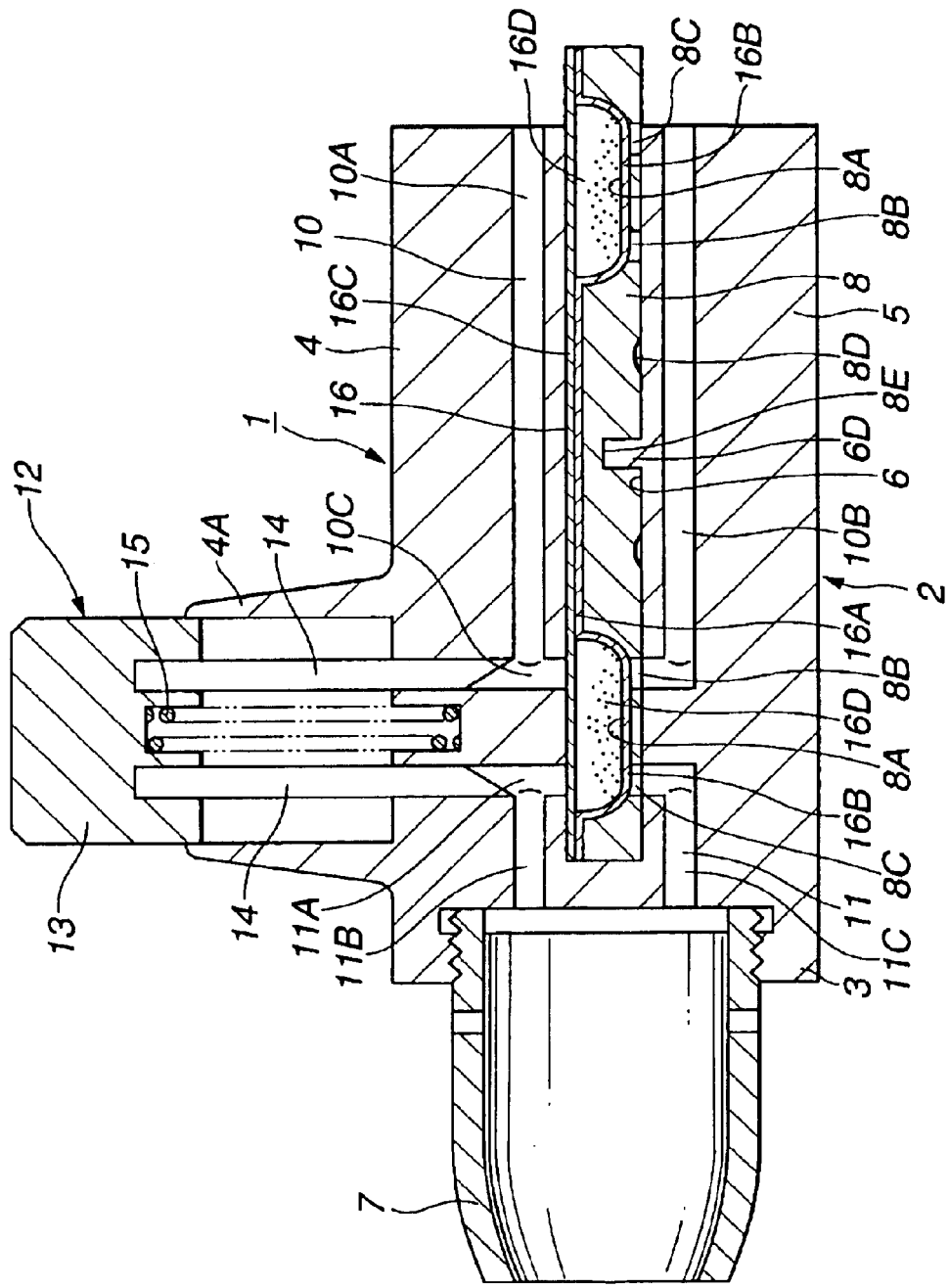
FIG. 9 is a longitudinal cross-sectional view illustrating the inhalant medicator in a state where the blister pack is installed on the holder of FIG. 6 and then the holder is mounted in a holder mounting groove formed in the medicator body of the inhalant medicator shown in FIG. 1.

Referring now to FIGS. 8 and 9, there is shown the detailed structure of the blister pack 16 applied to the inhalant medicator of the first embodiment. As shown in FIGS. 8 and 9, blister pack 16 is comprised of base panel 16A and lid panel 16C affixed onto the principal surface (or the obverse) of base panel 16A. The base panel 16A has a thin-walled disc shape and is made of synthetic resin, aluminum material, or the like. As best seen in FIG. 8, the base panel 16A has a plurality of blistered portions 16B, 16B, ..., 16B (in the first embodiment, eight blistered portions) around its entire circumference. On the other hand, the lid panel 16C has a thin-walled disc shape and is made of synthetic resin, aluminum material, or the like. The blistered portions 16B formed in the base panel 16A are located near the circumference of the base panel 16A, and formed as eight radially-elongated, substantially semi-cylindrical convex portions. The eight blistered portions 16B are circumferentially spaced apart from each other by 45degrees. By hermetically covering or closing the base panel 16A having eight blistered portions 16B by the lid panel 16C, eight medical powder storage chambers 16D are defined between the eight blistered portions 16B of base panel 16A and the lid panel 16C. Actually, a predetermined amount of medical powder, such as granular medicine or powdered medicine is stored in each of the medical powder storage chambers 16D.

The inhalant medicator of the first embodiment is constructed as previously discussed. Hereinbelow described in detail in reference to FIGS. 9–11 are the preliminary operation of inhalant medication through which a patient inhales medical powder, and the flow of air and the flow of medical powder during inhalation.

First of all, blister pack holder 8 is removed from the holder mounting groove 6 of medicator body 2. During removal of the holder 8, the guide groove 8E, formed in the underside of the holder and radially outwardly extending from the center of the holder, must be axially aligned with respect to the axis of the medicator body 2 under a condition in which the outermost end of guide groove 8E faces the inhalant port 7. Then, the holder 8 can be removed from the medicator body 2 by pulling the holder 8 against the bias produced by the two spring-loaded balls 9B of the positioning mechanism 9. Then, blister pack 16 is fitted to and installed on the upside of holder 8, such that eight blistered portions 16B of the blister pack are fitted to respective recessed fit portions 8A of the holder 8. At this time, by fitting the blistered portions 16B (the medical powder storage chambers 16D) to the respective recessed fit portions 8A, the blister pack 16 can be integrally connected to and reliably positioned with respect to the holder 8, and thus the blister pack 16 is rotatable together with the holder 8. After the blister pack 16 has been installed on the holder 8, the holder 8 is mounted into the holder mounting groove 6. In this case, the guide groove 8E must be aligned with the axis of the medicator body 2 so that the outermost end of the guide groove 8E is directed toward the inhalant port 7, and also the protruded portion 6D must be engaged with the guide groove 8E. In this manner, after the holder 8 has been completely pushed into the holder mounting groove 6 until the innermost end of the guide groove 8E engages with the protruded portion 6D, two balls (9B, 9B) of the positioning mechanism 9 are engaged with the two diametrically-opposed, small recessed fit portions 8D of the holder 8 by rotating the holder 8 in an arbitrary direction. By way of a series of preliminary setting operations as discussed above, as shown in FIG. 9, it is possible to accurately position one of the medical powder storage chambers 16D of blister pack 16 at the predetermined pricking position (the set position for inhalant medication).

Hereunder described in detail is the actual operation of inhalant medication made by virtue of breathing action of a patient. First of all, in order to prick holes in the blister pack 16 held at the predetermined pricking position, the support portion 13 of pricking tool 12 is pushed or depressed.

Figure 10:
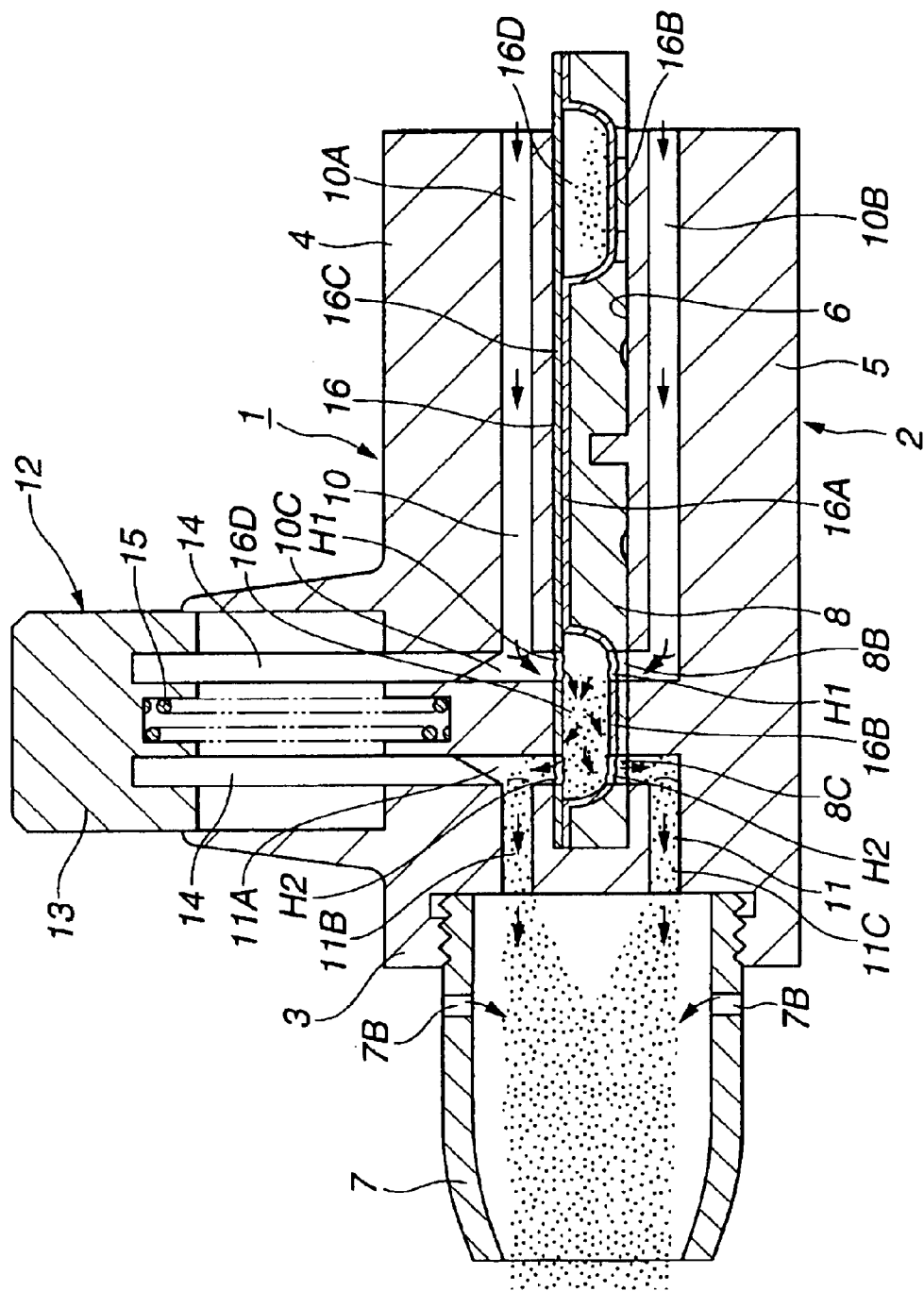
FIG. 10 is a longitudinal cross-sectional view illustrating the inhalant medicator in a state where medical powder stored in the storage chamber of the blister pack (16) installed on the holder of FIG. 6 is inhaled.
Figure 11:
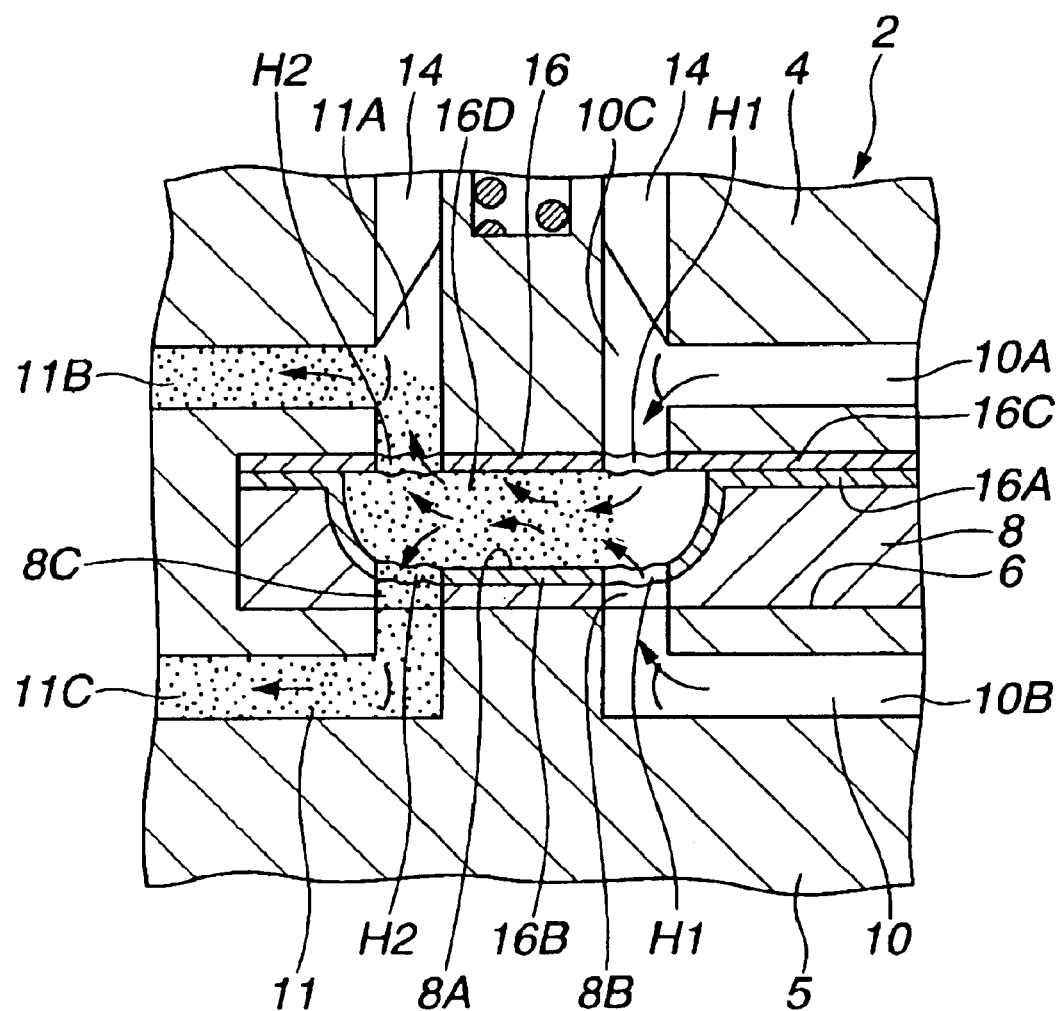
FIG. 11 is a partly enlarged longitudinal cross-sectional view showing air flow and medical powder flow in the medical powder storage chamber (16D) of the blister pack (16) installed on the holder of FIG. 6.
Figure 12:
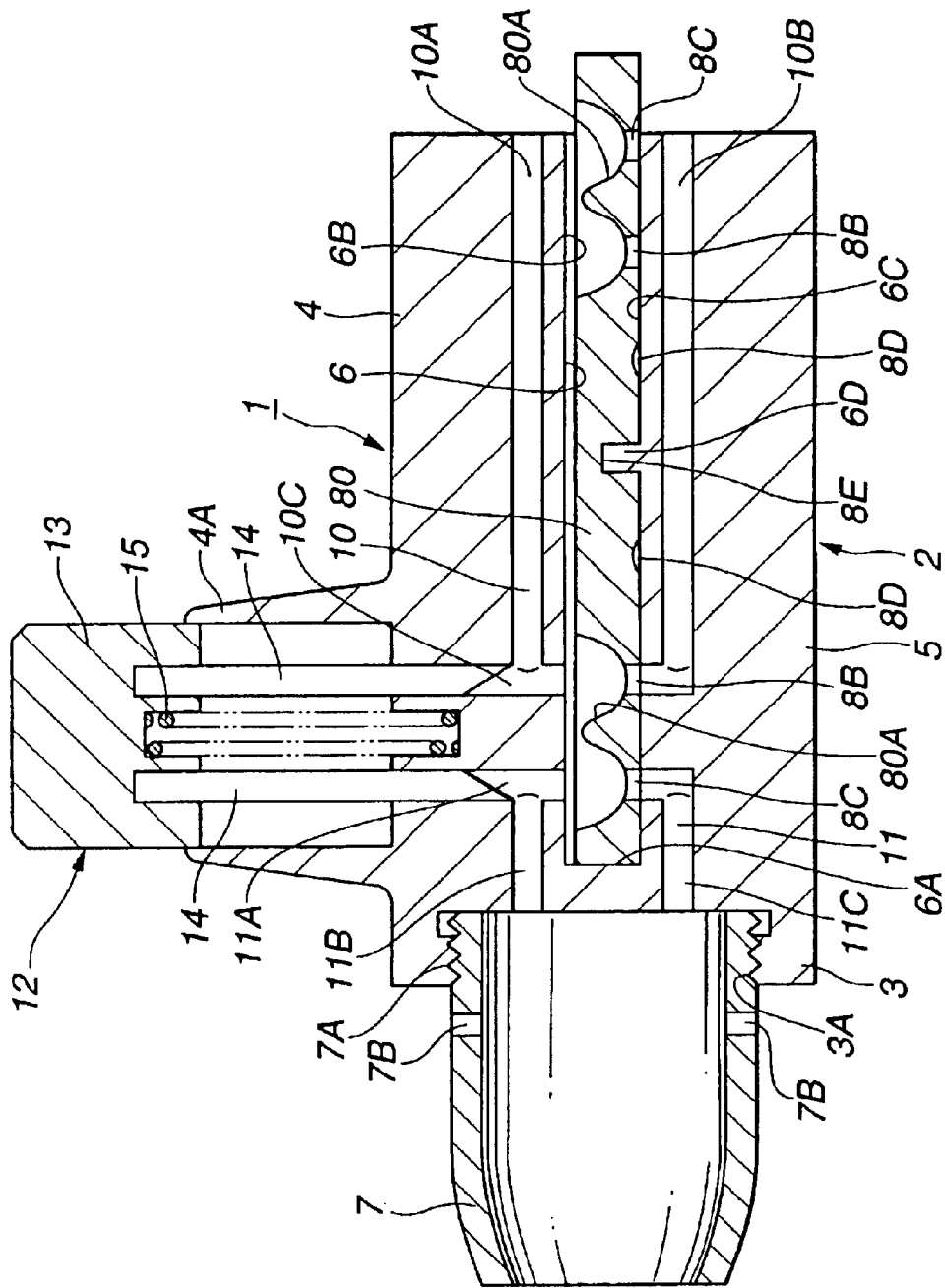
FIG. 12 is a longitudinal cross-sectional view illustrating another embodiment of an inhalant medicator with a blister pack holder having a cross section different from that shown in FIG. 1.
Figure 13:
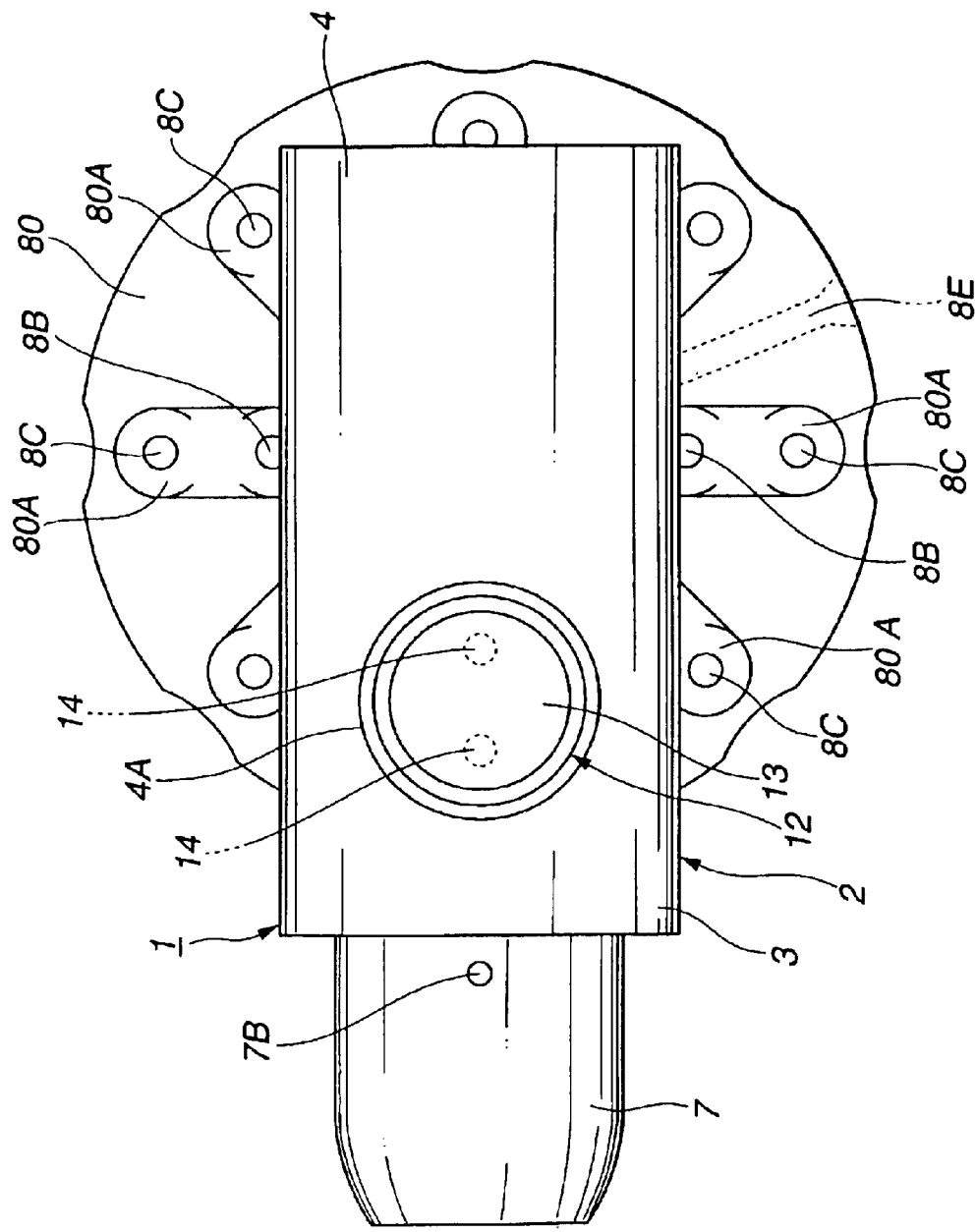
FIG. 13 is a plan view illustrating the inhalant medicator of the embodiment shown in FIG. 12.
Figure 14:
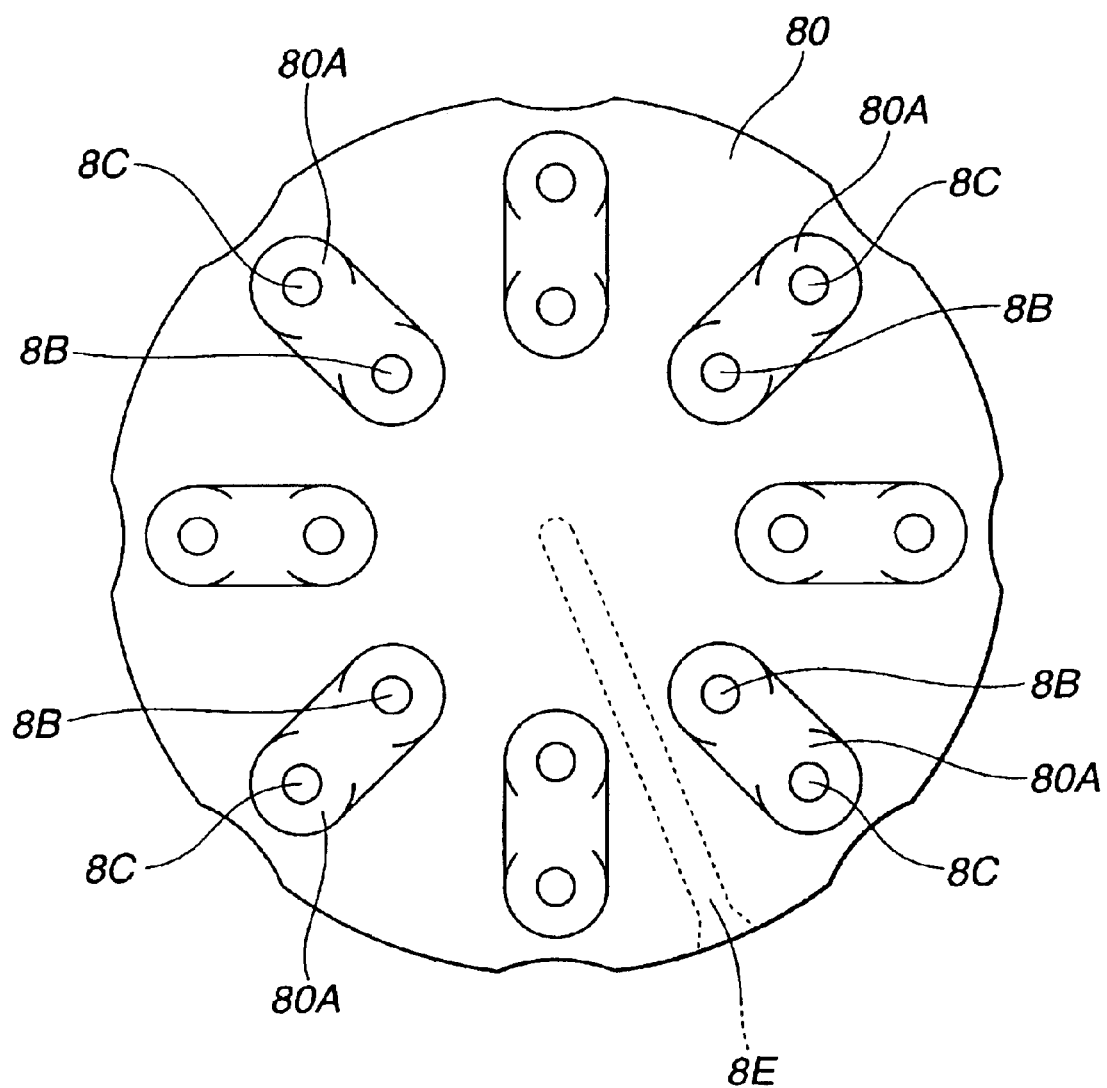
FIG. 14 is a plan view illustrating a blister pack holder (80) mounted on the medicator body of the inhalant medicator shown in FIG. 12.

As shown in FIGS. 10 and 11, two opposed inflow holes (H1, H1) communicating inflow air passageway 10 are pricked in the blistered portion 16B of base panel 16A and in the lid panel 16C by means of one of the two pins (14, 14) inserted into the pin insertion hole 10C, and at the same time two opposed outflow holes (H2, H2) communicating outflow air passageway 11 are pricked in the blistered portion 16B of base panel 16A and in the lid panel 16C by means of the other pin 14 inserted into the pin insertion hole 11A. As a result, the medical powder storage chamber 16D of blister pack 16 is communicated through the inflow holes (H1, H1) with the inflow air passageway 10, and also communicated through the outflow holes (H2, H2) with the outflow air passageway 11.

Under these conditions, when the patient draws his or her breath while taking the inhalant port 7 in his or her mouth, air (atmosphere) passes through the inflow air passageway 10 via the two inflow holes (H1, H1) and then flows into the medical powder storage chamber 16D.

At this time, the air flow introduced via the inflow holes (H1, H1) into the medical powder storage chamber 16D is brought into collision with the inner wall surface of medical powder storage chamber 16D, because the inflow holes (H1, H1) and the outflow holes (H2, H2) are spaced apart from each other in the axial direction of the medicator body (or in the longitudinal direction of the blistered portion of the blister pack) by a distance between the two pin insertion holes 8B and 8C, thereby resulting in turbulent flow within the medical powder storage chamber 16D. Thus, the medical powder stored in the chamber 16D can be effectively diffused or micronized by means of the turbulent flow.

As a consequence, it is possible to effectively flow out almost all of the medical powder pre-stored in the storage chamber 16D through the outflow holes (H2, H2) and the outflow air passageway 11 into the inhalant port 7 by virtue of the turbulent air flow. As discussed above, during breathing action, the patient can inhale a specified amount of medical powder via his or her oral cavity and trachea into lungs with the aid of the turbulent air flow. In this manner, the first inhalant medication can be completed.

Subsequently to the above, when the second inhalant medication is needed, the holder 8 is first rotated from the current angular position by 45 degrees. The next diametrically-opposed recessed fit portions 8D of holder 8 are thus engaged with the two spring-loaded balls 9B of positioning mechanism 9. After this, through the previously-noted pricking operation and inhaling operation, it is possible to inhale medical powder pre-stored in the other medical powder storage chamber 16D.

In this manner, eight inhalant medications in total can be continuously made. After the eight inhalant medications in total have been made, the holder 8 is removed from the medicator body 2, and then the old blister pack is replaced with a new blister pack for the next inhalation medication.

As set forth above, according to the inhalant medicator of the first embodiment, the inflow holes (H1, H1) communicating the inflow air passageway 10 and the outflow holes (H2, H2) communicating the outflow air passageway can be formed or pricked in the blister pack by means of two pins (14, 14) fixedly connected to the pricking tool 12, so that the inflow holes (H1, H1) and the outflow holes (H2, H2) are spaced apart from each other by a predetermined distance corresponding to a distance between the axes of two pins (14, 14). As a result of this, air flowing via the inflow holes (H1, H1) toward the outflow holes (H2, H2) is not directed straight, but brought into collision with the inner wall of the medical powder storage chamber. Turbulent air flow is thus produced within the medical powder storage chamber by the air flow directed from two inflow holes (H1, H1) via the internal space of the medical powder storage chamber to two outflow holes (H2,H2). Therefore, it is possible to effectively diffuse or micronize medical powder stored in the medical powder storage chamber by virtue of the turbulent air flow occurring in the medical powder storage chamber owing to the two inflow holes and two outflow holes pricked in both the base panel and lid panel of the blister pack by the two parallel pins during inhalation treatment of air/medical powder mixture. As a result of this, it is possible to efficiently reliably prescribe a specified amount of medical powder pre-stored in one of storage chambers 16D into lungs of a patient by way of breathing action. This enhances medical benefits of the medical powder, thereby enhancing the reliability of the inhalant medicator. Furthermore, the holder 8 is formed on its underside with the recessed fit portions 8D, and additionally the positioning mechanism 9 is provided in the holder mounting groove 6 for positioning the medical powder storage chamber 16D of blister pack 16 at the predetermined pricking position (the set position for inhalant medication) by fitting the spring-loaded balls (9B, 9B) to the recessed fit portions (8D, 8D). Thus, it is possible to easily accurately position the medical powder storage chamber 16D of blister pack 16 at the predetermined pricking position. In other words, it is possible to accurately prick holes (H1, H1, H2, H2) in the blistered portion of base panel 16A of blister pack 16 and in the lid panel 16C, thus ensuring easy handling of the inhalant medicator. Moreover, in the inhalant medicator assembly 1 of the first embodiment, the medicator body 2 is constructed by not only upper and lower medicator-body portions 4 and 5, but also joining portion 3 interconnecting the upper and lower medicator-body portions 4 and 5, and also the holder mounting groove 6 is simply defined between the upper and lower medicator-body portions. Such a holder mounting groove structure is so simple. The inhalant medicator of the embodiment is designed to be easily assembled by mounting the disc-shaped blister pack holder 8 into the holder mounting groove 6 being simple in structure, thus reducing the number of parts of the inhalant medicator assembly. This ensures ease of assembly, and also reduces total production costs of the inhalant medicator. Additionally, the disc-shaped holder 8 is formed on its upside with circumferentially equally spaced, radially-elongated eight recessed fit portions 8A (eight substantially semi-cylindrical cavities). Thus, it is possible to accurately easily position the blister pack 16 on the holder 8 by fitting the blistered portions 16B to the respective recessed fit portions 8A, thus allowing the blister pack 16 to integrally rotate together with the holder 8. This ensures ease of handling. In addition to the above, the holder 8 is formed on its underside with the guide groove 8E which is engageable with the protruded portion 6D of holder mounting groove 6. The guide groove 8E permits the protruded portion 6D to be reliably easily guided to the rotation center of the holder 8 (the innermost end of the guide groove 8E). This ensures accurate and easy mounting of the holder 8 on the desired position of the medicator body 2. thus ensuring ease of handling.

Referring now to FIGS. 12 through 19, there are shown the inhalant medicator of the second embodiment and a blister pack 21 applied to the inhalant medicator of the second embodiment. The inhalant medicator of the second embodiment of FIGS. 12–19 is similar to the first embodiment of FIGS. 1–11, except that the shape of the blister pack holder 80 and the shape of the blister pack 21 of the second embodiment are different from those of the first embodiment. Thus, the same reference signs used to designate elements in the first embodiment shown in FIGS. 1–11 will be applied to the corresponding elements used in the second embodiment shown in FIGS. 12–19, for the purpose of comparison of the first and second embodiments. The blister pack 21 and its holder 80 of the second embodiment will be hereinafter described in detail with reference to the accompanying drawings, while detailed description of elements denoted by the same reference signs will be omitted because the above description thereon seems to be self-explanatory.

Figure 15:
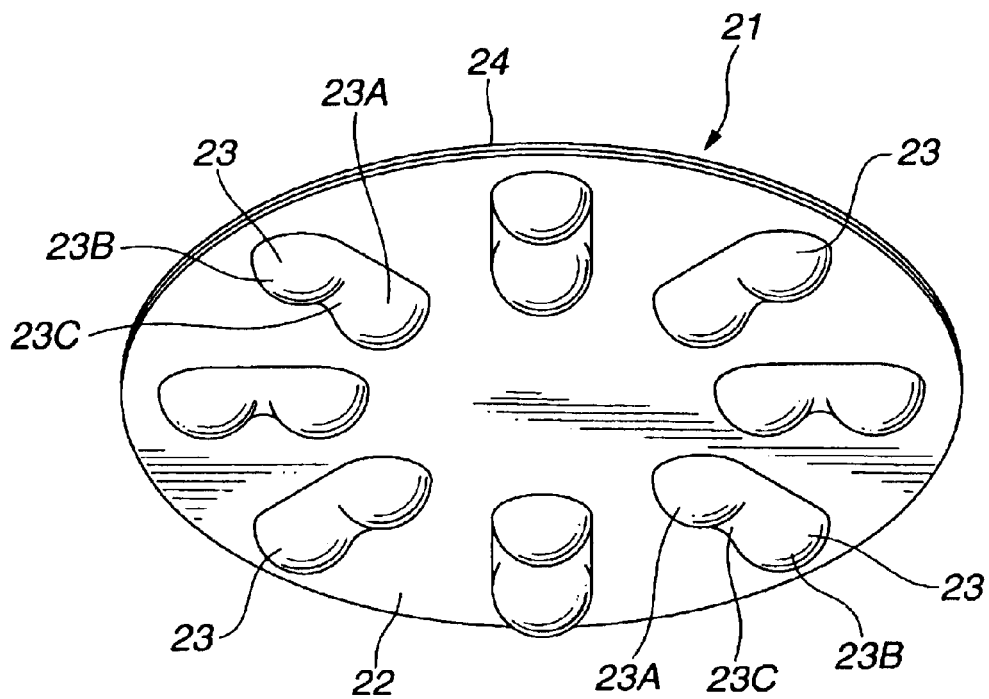
FIG. 15 is a perspective view of a blister pack (21) to be installed on the holder of FIG. 14, as viewed from its bottom side (its base panel side).
Figure 16:
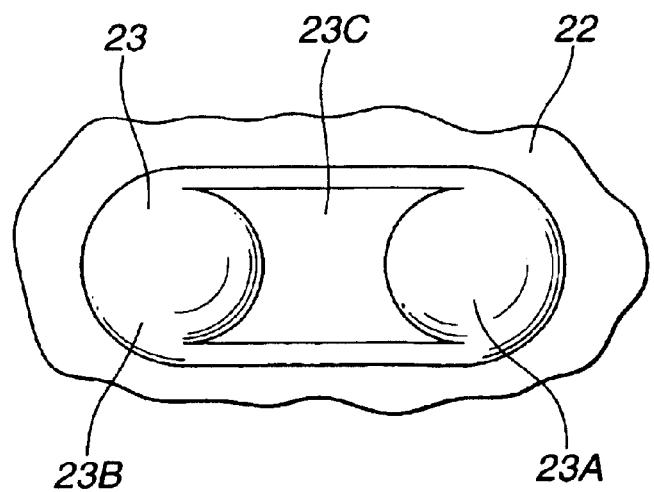
FIG. 16 is a bottom view illustrating details of one blistered portion (23) of the blister pack (21) installed on the holder of FIG. 14.
Figure 17:
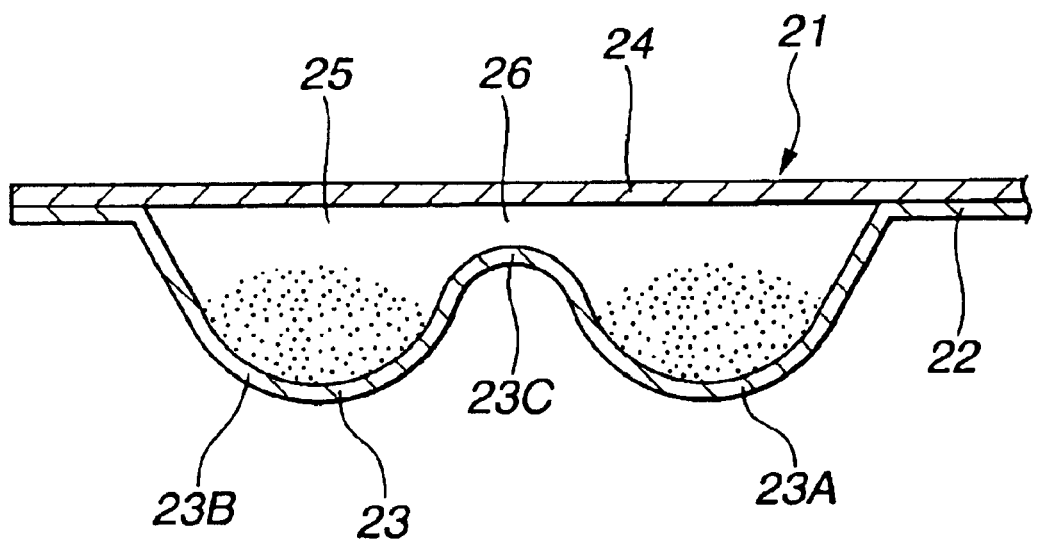
FIG. 17 is a partly enlarged longitudinal cross-sectional view showing the blistered portion (23), a medical-powder storage chamber (25), and a flow-constriction passage (26).
Figure 18:
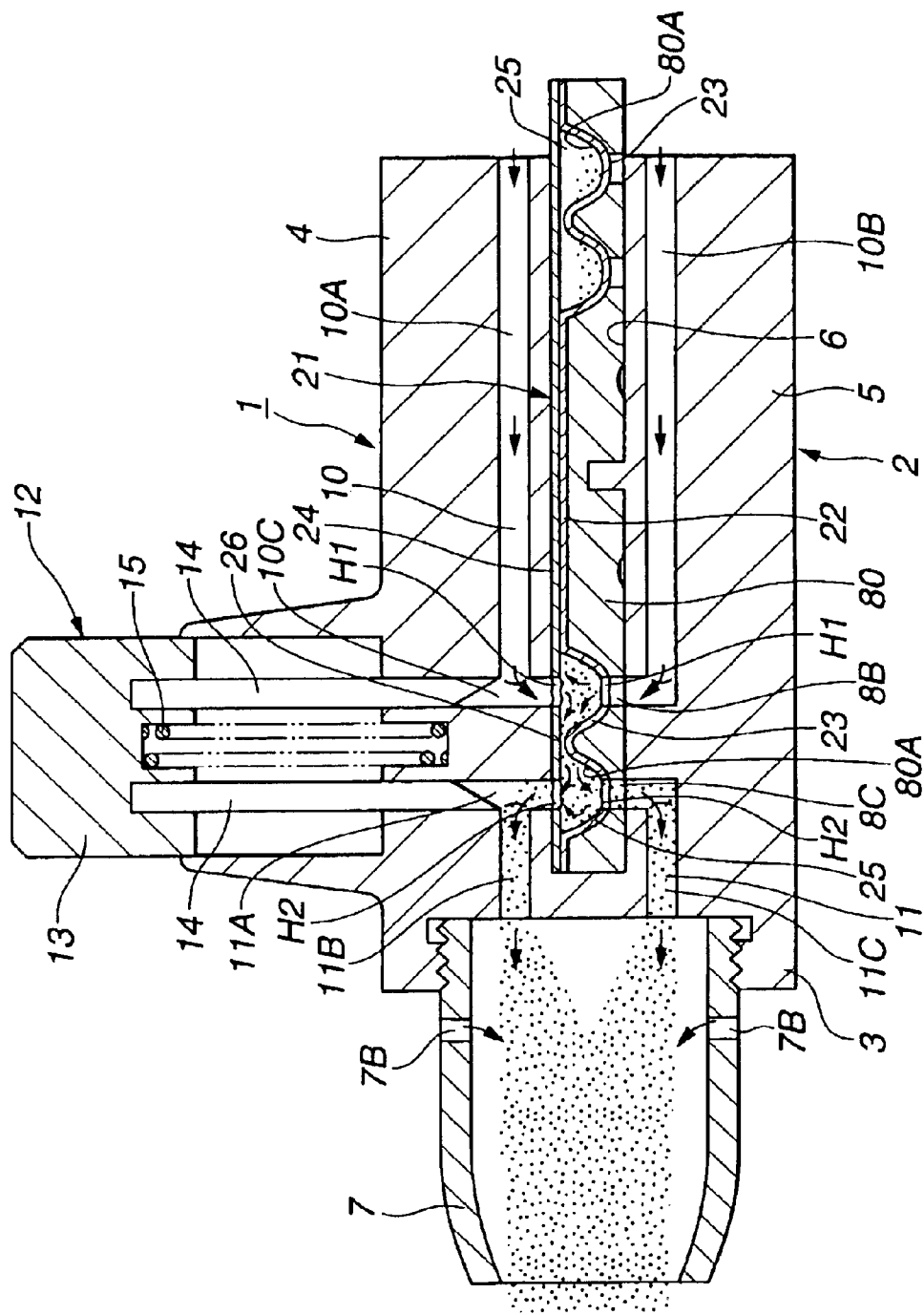
FIG. 18 is a longitudinal cross-sectional view illustrating the inhalant medicator in a state where medical powder stored in the storage chamber of the blister pack (21) installed on the holder of FIG. 14 is inhaled.
Figure 19:
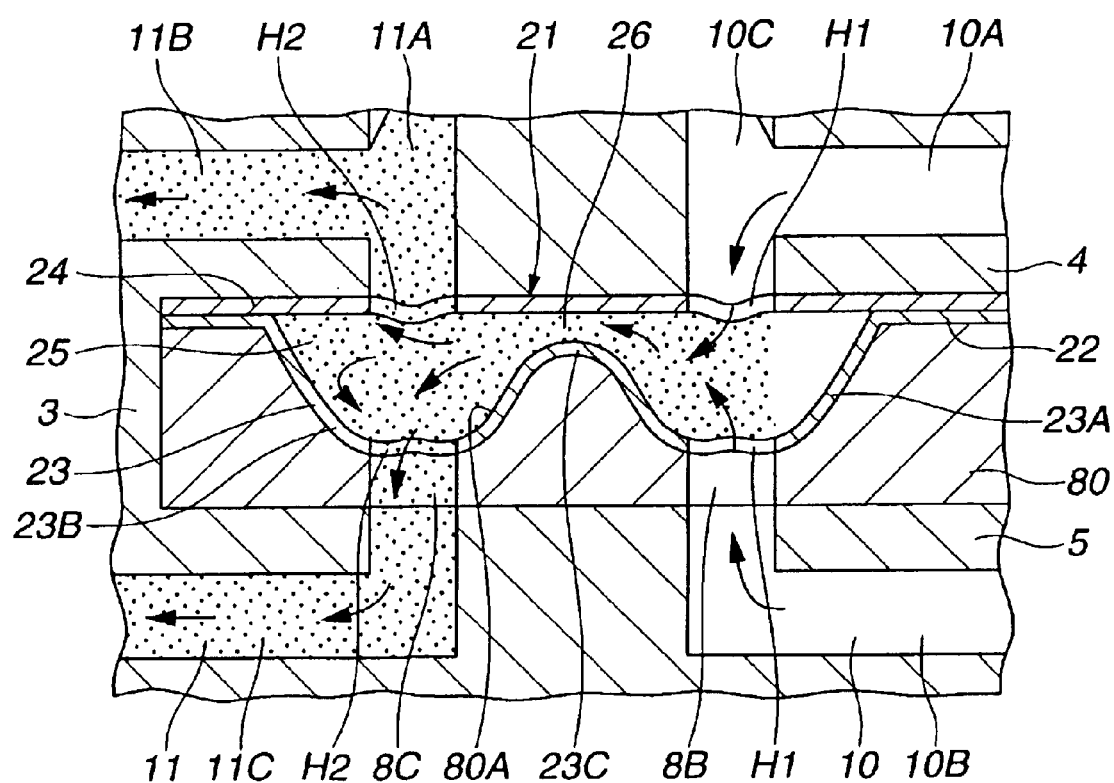
FIG. 19 is a partly enlarged longitudinal cross-sectional view showing air flow and medical powder flow in the medical powder storage chamber (25) of the blister pack (21) installed on the holder of FIG. 14.

As best seen in FIGS. 15 through 17, blister pack 21 is comprised of a base panel 22, a lid panel 24, a medical powder storage chamber 25, and a flow-constriction passage 26. Base panel 22 has a thin-walled disc shape and is made of synthetic resin, aluminum material, or the like. The base panel has a plurality of blistered portions 23, 23, . . . , 23 (in the second embodiment, eight blistered portions) around its entire circumference. On the other hand, lid panel 24 has a thin-walled disc shape and is made of synthetic resin, aluminum material, or the like. The eight blistered portions 23 are circumferentially spaced apart from each ther by 45 degrees. As best seen in FIGS. 16 and 17, the blistered portions 23 formed in the base panel 22 are located near the circumference of the base panel 22, and formed as eight radially-elongated, substantially elliptical convex portions. Each of the blistered portions 23 includes a radially-inward, substantially hemispherical convex portion 23A and a radially-outward, substantially hemispherical convex portion 23B, and a flow-constriction portion 23C formed between the two hemispherical convex portions 23A and 23B. The flow-constriction portion 23C is configured to provide a flow-constriction orifice passage 26 between the base panel 22 and the lid panel 24 at a connecting point between two convex portions 23A and 23B in close proximity to the inner wall of the lid panel 24. By hermetically covering or closing the base panel 22 having eight blistered portions 23 by the lid panel 24, eight medical powder storage chambers 25 are defined between the eight blistered portions 23 of base panel 22 and the lid panel 24. A predetermined amount of medical powder is stored in each of the medical powder storage chambers 24. The flow-constriction orifice passage 26 is formed in the medical powder storage chamber 25 and arranged between the previously-described inflow holes (H1, H1) and outflow holes (H2, H2). The flow-constriction orifice passage 26 functions to increase the flow velocity of air flowing from the inflow holes (H1, H1) via the interior of the medical powder storage chamber 25 to the outflow holes (H2, H2). Additionally, the flow-constriction orifice passage 26 functions to cause proper turbulent flow within the medical powder storage chamber 25 and consequent mixing action. By suitably varying or selecting the orifice size of the flow-constriction orifice passage 26 depending on characteristics or properties of medical powder used, such as a strong condensation, and a particle size, turbulent air flow suitable to properties of medical powder can be produced. Therefore, it is possible to effectively diffuse the medical powder by virtue of the flow-constriction orifice passage 26 which is dimensioned and designed to be suitable for the properties of medical powder stored in the storage chamber 25. On the other hand, the holder 80 is formed on its upside with eight recessed fit portions 80A, 80A, . . . , 80A circumferentially spaced apart from each other by 45 degrees and located near its circumference. In the inhalant medicator of the second embodiment, the eight recessed fit portions 80A are configured or formed as eight radially-elongated, substantially elliptical cavities. Eight blistered portions 23 of blister pack 21 are integrally fitted into the respective eight recessed fit portions 80A of holder 80.

In the same manner as the inhalant medicator of the first embodiment, when inhalant medication is initiated using the inhalant medicator of the second embodiment, first, the preliminary operation of inhalant medication is made. Inflow holes (H1, H1) and outflow holes (H2, H2) are pricked in the blistered portion 23 of base panel 22 and in the lid panel 24 of blister pack 21 held at the predetermined pricking position, after a series of preliminary setting operations have been completed.

Under these conditions, when the patient draws his or her breath while taking the inhalant port 7 in his or her mouth, air flows through the inflow air passage 10 and the inflow holes (H1, H1) into the storage chamber 25. At this time, air flow directed from the inflow holes (H1, H1) to the outflow holes (H2, H2) passes through the flow-constriction orifice passage 26. By means of the orifice passage 26, the flow velocity of air flow passing through the orifice passage 26 is increased, and thus causing properly strengthened turbulent flow (see FIGS. 18 and 19). Therefore, the strengthened turbulent flow can effectively diffuse or micronize the medical powder.

As a result of this, it is possible to effectively flow out almost all of medical powder pre-stored in the storage chamber 25 through the outflow holes (H2, H2) and the outflow air passageway 11 into the inhalant port 7 by virtue of the properly-strengthened turbulent air flow. Thus, during breathing action, the patient can inhale a specified amount of medical powder via his or her oral cavity and trachea into lungs by way of the properly-strengthened turbulent air flow.

As discussed above, according to the inhalant medicator of the second embodiment, the flow-constriction orifice passage 26 is defined within the medical powder storage chamber 25 of blister pack 21 by the flow-constriction portion 23C of blistered portion 23 so that the flow-constriction orifice passage 26 is located between the inflow holes (H1, H1) and the outflow holes (H2, H2). The flow-constriction orifice passage 26 acts to properly regulate or control the air flow passing through the medical powder storage chamber 25 depending on the properties or characteristics peculiar to medical powder stored in the storage chamber 25. Therefore, it is possible to produce turbulent air flow suitable for medical powder stored in the storage chamber 25 by properly determining or setting an orifice size of the flow-constriction orifice passage 26 in due consideration of characteristics or properties of the medical powder, such as a particle size (fine powder or granule), a condensation property (strong condensation or weak condensation), an amount of a dose of medical powder, or the like. Therefore, it is possible to reliably effectively prescribe a specified amount of medical powder toward within lungs of the patient. This enhances medical benefits of the medical powder, and also enhances the reliability of the inhalant medicator. Additionally, the blister pack 21, storing medical powder, has its own flow-constriction orifice passage 26 in each of the blistered portions (or in each of the medical powder storage chambers). Thus, it is possible to easily form a flow-constriction orifice passage suitable for every kind of medical powder, and thereby an efficiency of inhalant medication can be remarkably enhanced.

Referring now to FIGS. 20 through 23, there is shown the modified blister pack 31. As detailed hereunder, the modified blister pack 31 shown in FIGS. 20–23 is characterized by a deeply-recessed medical powder collecting portion 34, as viewed from the cross section shown in FIG. 21. The blister pack 31 is comprised of base panel 32, medical powder collecting portion 34, lid panel 35, and medical powder storage chamber 36.

Figure 20:
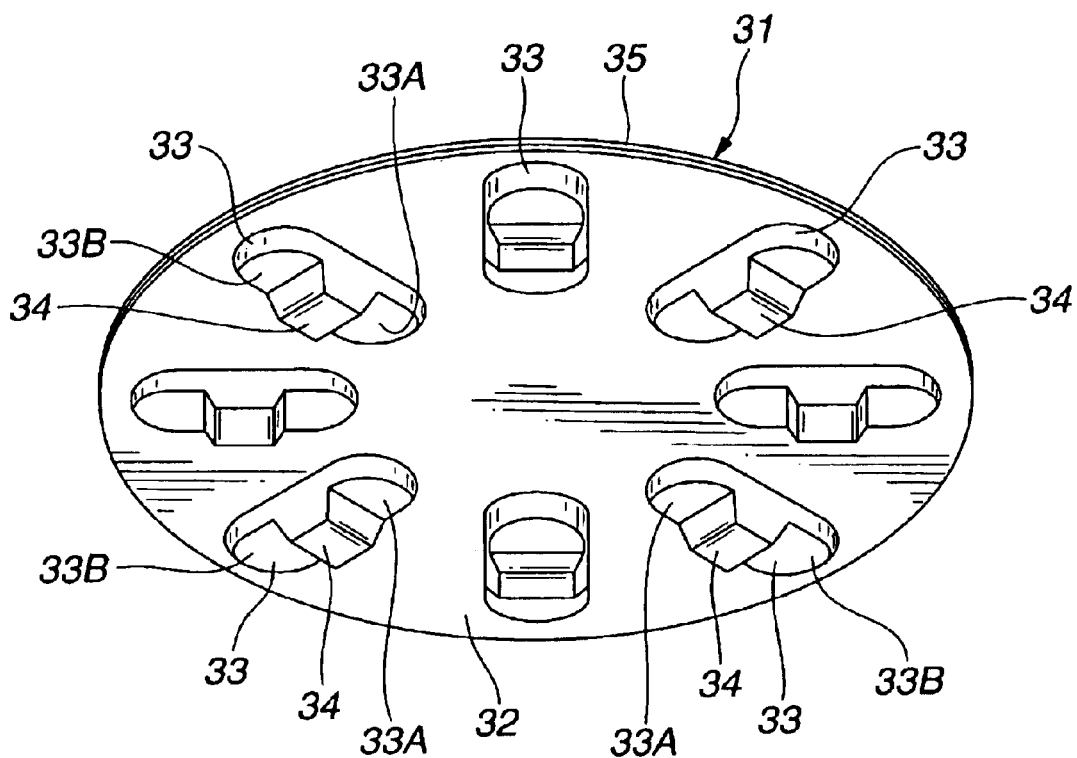
FIG. 20 is a perspective view of a modified blister pack (31), as viewed from its bottom side (its base panel side).

The base panel 32 has a thin-walled disc shape and is made of synthetic resin, aluminum material, or the like. As best seen in FIG. 20, the base panel 32 has a plurality of blistered portions 33, 33, . . . , 33 (eight blistered portions) around its entire circumference. The shape and material of the lid panel 35 of blister pack 31 are identical to those of blister pack 16 applied to the inhalant medicator of the first embodiment (or to those of blister pack 21 applied to the inhalant medicator of the second embodiment).

Figure 21:
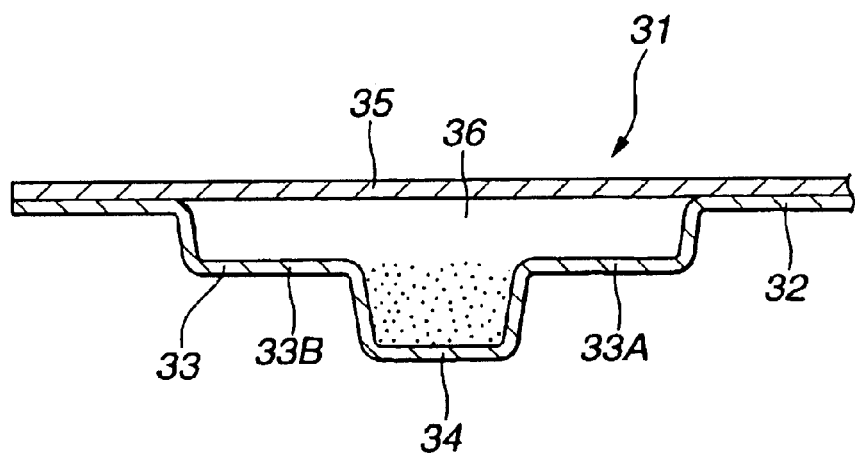
FIG. 21 is a partly enlarged longitudinal cross-sectional view showing a blistered portion (33), a medical-powder storage chamber (36), and a medical powder collecting portion (34).

The modified blister pack 31 shown in FIGS. 20–23 is different from the blister pack 21 shown in FIGS. 15–17, in that the shape of each blistered portion 33 of base panel 32 differs from the shape of each blistered portion 23 of base panel 22. As best seen in FIG. 21, the blistered portions 33 are formed as eight radially-elongated, substantially elliptical convex portions. Each of the blistered portions 33 includes a radially-inward, shallow pricked portion 33A in which the previously-noted inflow hole H1 is pricked, and a radially-outward, shallow pricked portion 33B in which the previously-noted outflow hole H2 is pricked.

The medical powder collecting portion 34 is deeply formed or recessed in the base panel 32 midway between the radially-inward, shallow pricked portion 33A and the radially-outward, shallow pricked portion 33B. The medical powder collecting portion 34 serves as an air-flow regulation means as described later. When the blister pack 31 is installed on the blister pack holder, the medical powder collecting portion 34 of the blistered portion 33 serves as a deeply-recessed medical powder collecting portion kept at a level lower than the shallow pricked portions (33A, 33B).

A portion denoted by reference sign 36 is the medical powder storage chamber defined between the blistered portion 33 of base panel 32 and the lid panel 35. A predetermined amount of medical powder is stored in the medical powder storage chamber 36, such that almost all of the medical powder is collected or pre-stored in the medical powder collecting portion 34.

Figure 22:
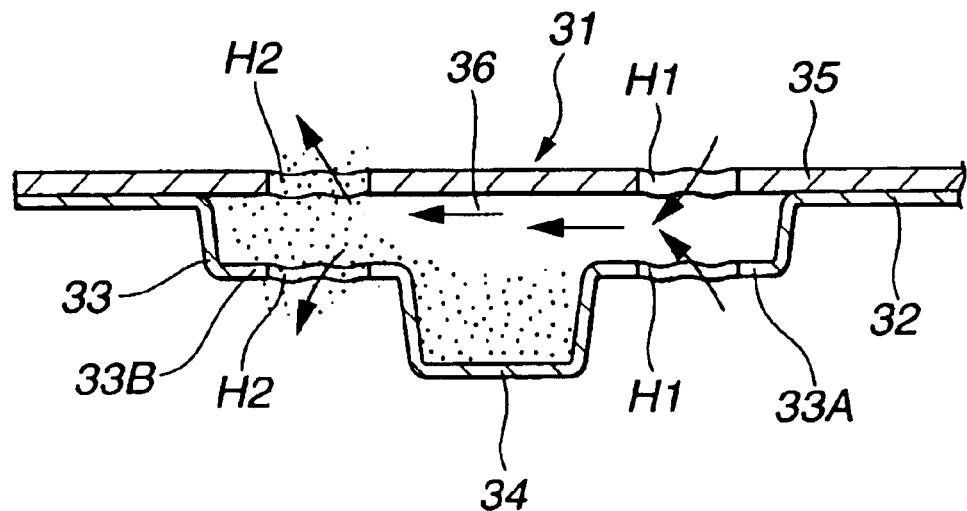
FIG. 22 is a partly enlarged longitudinal cross-sectional view showing air flow and medical powder flow in the medical powder storage chamber of the blister pack (31) of FIG. 20, during initial inhalation action.
Figure 23:
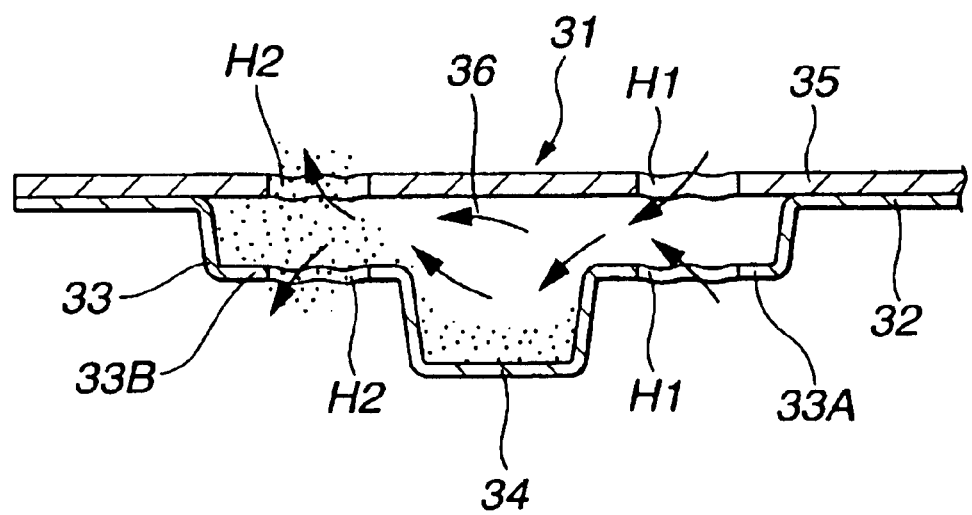
FIG. 23 is a partly enlarged longitudinal cross-sectional view showing air flow and medical powder flow in the medical powder storage chamber of the blister pack (31) in the middle of the inhalation action.

The blister pack 31 shown in FIGS. 20–23 is constructed as previously discussed. Hereinbelow described in detail in reference to FIGS. 22 and 23 are the flow of air passing through the medical powder storage chamber 36 and the flow of medical powder within the storage chamber 36 during inhalation. Inflow holes (H1, H1) and outflow holes (H2, H2) are pricked in the blistered portion 33 of base panel 32 and in the lid panel 34 of blister pack 31 held at the predetermined pricking position, after a series of preliminary setting operations have been completed.

Under these conditions, when the patient draws his or her breath while taking the inhalant port 7 in his or her mouth, at the initial stage of the inhaling action, air introduced through the inflow air passage 10 via the inflow holes (H1, H1) into the storage chamber 35, functions to fling up and diffuse a part of medical powder located at the top of the medical powder collecting portion 34 (see FIG. 22). The upflung and diffused portion of the medical powder collected in the collecting portion 34 is supplied into the outflow holes (H2, H2).

When several times of inhaling actions are repeated, the medical powder stored in the storage chamber 36 can be gradually reduced. At this time, as clearly shown in FIG. 23, air flow passing through the inflow holes (H1, H1) enters the medical powder collecting portion 34, and therefore medical powder collected in the collecting portion 34 is gradually flung up and diffused from the uppermost portion until a lowermost portion of the medical powder stored is flung up, and thus the diffused medical powder is supplied into the outflow holes (H2, H2) little by little.

As discussed above, according to the structure of the blister pack 31 having the deeply-recessed medical powder collecting portion 34, it is possible to fling up and uniformly diffuse the medical powder stored in the storage chamber 36 little by little. This prevents a large amount of air/medical powder mixture in one breath from being flown into the outflow holes (H2, H2), thus avoiding the outflow holes from being choked up with such a large amount of medical powder flow mass. In case that inhalant medication is made to a patient having a weak trachea, the patient can inhale the medical powder little by little. This prevents the patient from getting a fit of coughing during the inhalant medication, thus ensuring a stable medication during the breathing action.

Referring now to FIGS. 24 through 27, there is shown another modified blister pack 41. As detailed hereunder, the modified blister pack 41 shown in FIGS. 24–27 is characterized by a sloped surface 44, as viewed from the cross section shown in FIG. 25. The blister pack 41 is comprised of base panel 42, sloped surface 44, lid panel 45, and medical powder storage chamber 46.

The blistered portion 43 of blister pack 41 is formed with the previously-noted sloped surface 44 such that a side of the inflow holes (H1, H1) penetrating the radially-inward half of the blistered portion of base panel 42 is formed as a shallow portion, whereas a side of the outflow holes (H2, H2) penetrating the radially-outward half of the blistered portion of base panel 42 is formed as a deep portion.

Figure 24:
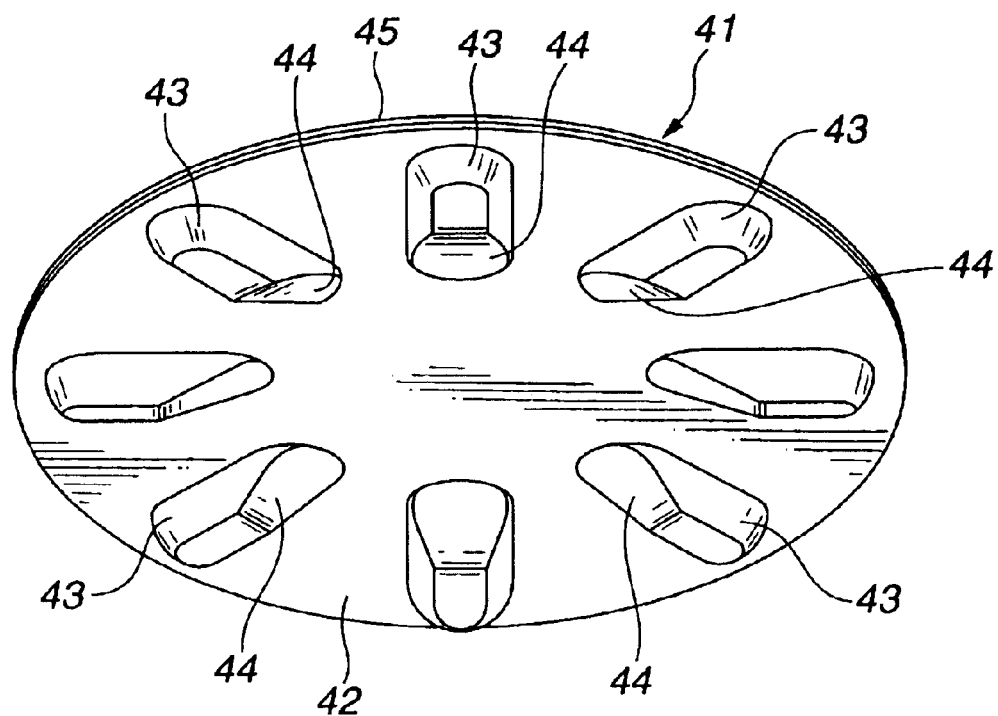
FIG. 24 is a perspective view of another modified blister pack (41), as viewed from its bottom side (its base panel side).

As best seen in FIG. 24, the base panel 42 has a plurality of blistered portions 43, 43, ..., 43 (eight blistered portions) around its entire circumference. The shape and material of the lid panel 45 of blister pack 41 are identical to those of blister pack 16 applied to the inhalant medicator of the first embodiment (or to those of blister pack 31 shown in FIGS. 20–23).

Figure 25:
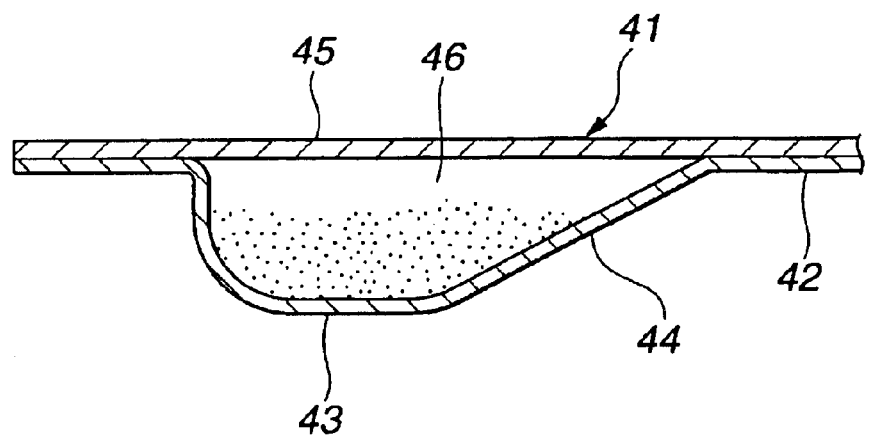
FIG. 25 is a partly enlarged longitudinal cross-sectional view showing a blistered portion (43), a medical-powder storage chamber (46), and a sloped surface (44).

The modified blister pack 41 shown in FIGS. 24–27 is different from the blister pack 21 shown in FIGS. 15–17, in that the shape of each blistered portion 43 of base panel 42 differs from the shape of each blistered portion 23 of base panel 22. As best seen in FIG. 25, the blistered portions 43 are formed as eight radially-elongated, substantially elliptical convex portions.

The radially-elongated inward half of the blistered portion 43 is formed as a comparatively shallow, sloped surface portion 44 (simply, a sloped surface), while the radially-elongated outward half of the blistered portion 43 is formed as a comparatively deep, recessed portion (simply, a deep recess), as viewed from the cross section shown in FIG. 25. In other words, the sloped surface 44 is dimensioned or sloped downwards (viewing FIG. 25) so that the convexity ratio of the blistered portion 43 radially increases from the inside to the outside. The inflow holes (H1, H1) are pricked in the sloped surface 44, while the outflow holes (H2, H2) are pricked in the deep recess.

The medical powder storage chamber 46 is defined between the blistered portion 43 of base panel 42 and the lid panel 45. A predetermined amount of medical powder is stored in the medical powder storage chamber 46, such that almost all of the medical powder is mainly stored in the deep recess corresponding to the outflow holes (H2, H2) by way of the sloped surface 44.

Figure 26:
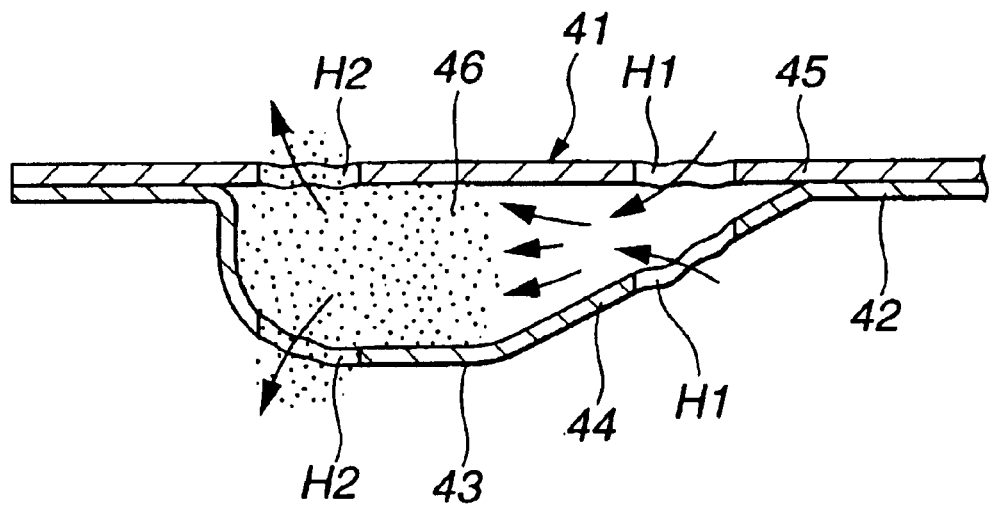
FIG. 26 is a partly enlarged longitudinal cross-sectional view showing air flow and medical powder flow in the medical powder storage chamber of the blister pack (41) of FIG. 24, during initial inhalation action.
Figure 27:
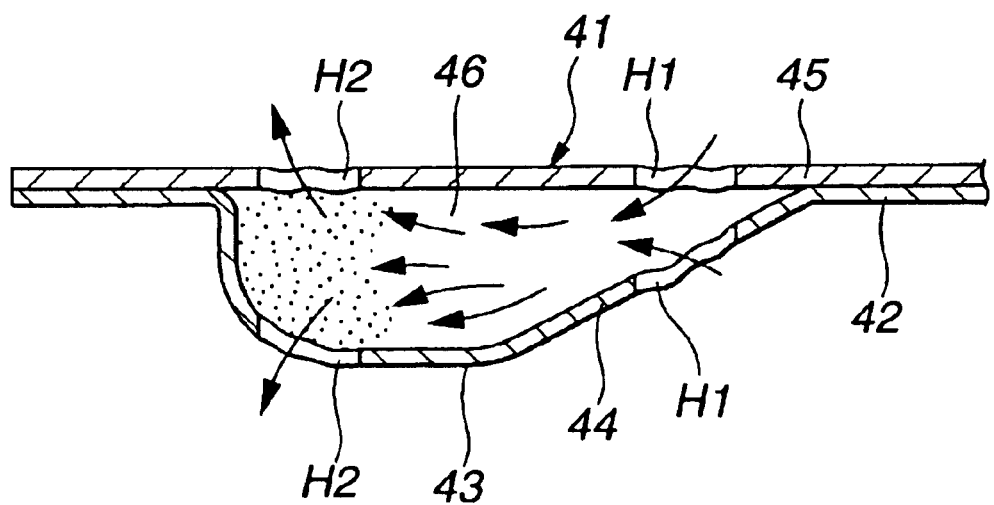
FIG. 27 is a partly enlarged longitudinal cross-sectional view showing air flow and medical powder flow in the medical powder storage chamber of the blister pack (41) in the middle of the inhalation action.

The blister pack 41 shown in FIGS. 24–27 is constructed as previously discussed. Hereinbelow described in detail in reference to FIGS. 26 and 27 are the flow of air passing through the medical powder storage chamber 46 and the flow of medical powder within the storage chamber 46 during inhalation. Inflow holes (H1, H1) and outflow holes (H2, H2) are pricked in the blistered portion 43 of base panel 42 and in the lid panel 44 of blister pack 41 held at the predetermined pricking position, after a series of preliminary setting operations have been completed.

Under these conditions, when a patient draws his or her breath while taking the inhalant port 7 in his or her mouth, at the initial stage of the inhaling action, air introduced through the inflow air passage 10 via the inflow holes (H1, H1) into the storage chamber 46, flows through the interior of the storage chamber in a manner so as to push out the medical powder toward within the outflow holes (H2, H2) while diffusing the medical powder mainly stored in the deep recess of the blistered portion 43 (see FIG. 26). Thus, the air introduced through the inflow holes (H1, H1) forcibly pushes the medical powder towards the outflow holes (H2, H2), and thus the medical powder stored in the storage chamber 46 is flown out of the outflow holes (H2, H2) at a breath (see FIG. 27).

According to the structure of the blister pack 41 having the sloped surface 44 at the inflow side thereof, it is possible to flow out the medical powder stored in the storage chamber 46 at a breath, such that the medical power accumulated around the outflow holes (H2, H2) is pushed out by way of air flow directed from the inflow holes (H1, H1) to the outflow holes (H2, H2). As a result, the patient can inhale the medical powder stored in the storage chamber 46 for a short time period. This reduces a burden on the patient's lungs. In particular, the blister pack 41 shown in FIGS. 24–27 is suitable to prescribe a relatively small amount of medical powder.

Referring now to FIGS. 28 through 31, there is shown another modified blister pack 51. As detailed hereunder, the modified blister pack 51 shown in FIGS. 28–31 is characterized by a sloped surface 54, as viewed from the cross section shown in FIG. 29. The blister pack 51 is comprised of base panel 52, sloped surface 54, lid panel 55, and medical powder storage chamber 56.

The blistered portion 53 of blister pack 51 is formed with the previously-noted sloped surface 54 such that a side of the outflow holes (H2, H2) penetrating the radially-outward half of the blistered portion of base panel 52 is formed as a shallow portion, whereas a side of the inflow holes (H1, H1) penetrating the radially-inward half of the blistered portion of base panel 52 is formed as a deep portion.

Figure 28:
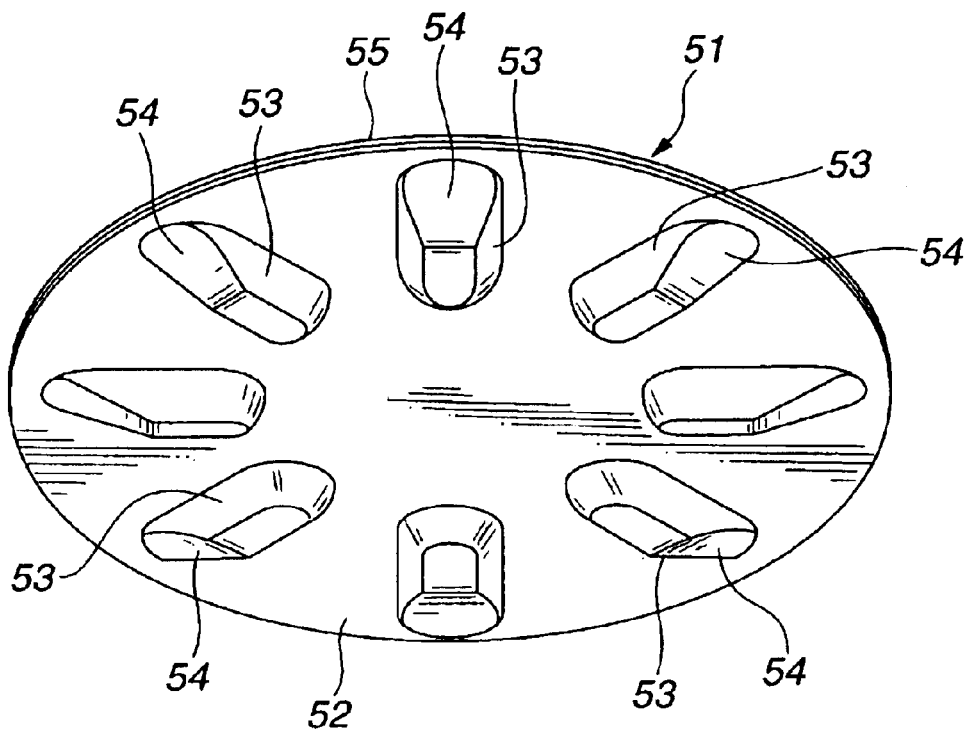
FIG. 28 is a perspective view of another modified blister pack (51), as viewed from its bottom side (its base panel side).

As best seen in FIG. 28, the base panel 52 has a plurality of blistered portions 53, 53, . . . , 53 (eight blistered portions) around its entire circumference. The shape and material of the lid panel 55 of blister pack 51 are identical to those of blister pack 16 applied to the inhalant medicator of the first embodiment (or to those of blister pack 31 shown in FIGS. 20–23).

Figure 29:
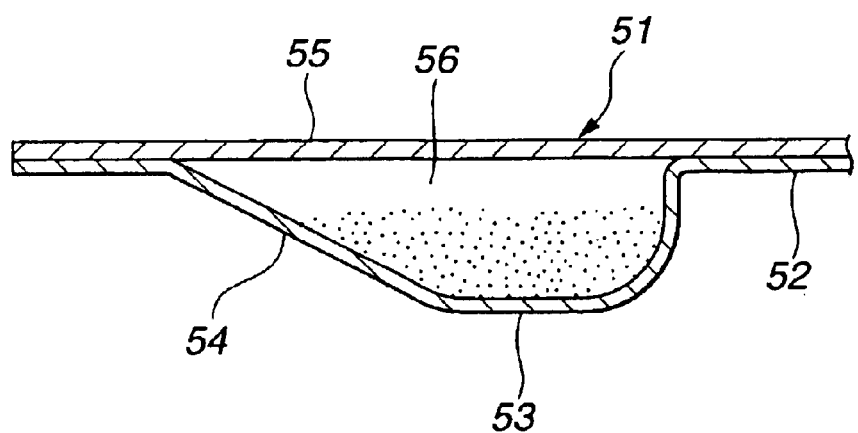
FIG. 29 is a partly enlarged longitudinal cross-sectional view showing a blistered portion (53), a medical-powder storage chamber (56), and a sloped surface (54).

The modified blister pack 51 shown in FIGS. 28–31 is different from the blister pack 21 shown in FIGS. 15–17, in that the shape of each blistered portion 53 of base panel 52 differs from the shape of each blistered portion 23 of base panel 22. As best seen in FIG. 29, the blistered portions 53 are formed as eight radially-elongated, substantially elliptical convex portions.

The radially-elongated outward half of the blistered portion 53 is formed as a comparatively shallow, sloped surface portion 54 (simply, a sloped surface), while the radially-elongated inward half of the blistered portion 53 is formed as a comparatively deep, recessed portion (simply, a deep recess), as viewed from the cross section shown in FIG. 29. In other words, the sloped surface 54 is dimensioned or sloped upwards (viewing FIG. 25) so that the convexity ratio of the blistered portion 53 radially decreases from the inside to the outside.

The outflow holes (H2, H2) are pricked in the sloped surface 54, while the inflow holes (H1, H1) are pricked in the deep recess. The medical powder storage chamber 56 is defined between the blistered portion 53 of base panel 52 and the lid panel 55. A predetermined amount of medical powder is stored in the medical powder storage chamber 56, such that almost all of the medical powder is mainly stored in the deep recess corresponding to the inflow holes (H1, H1) by way of the sloped surface 54.

Figure 30:
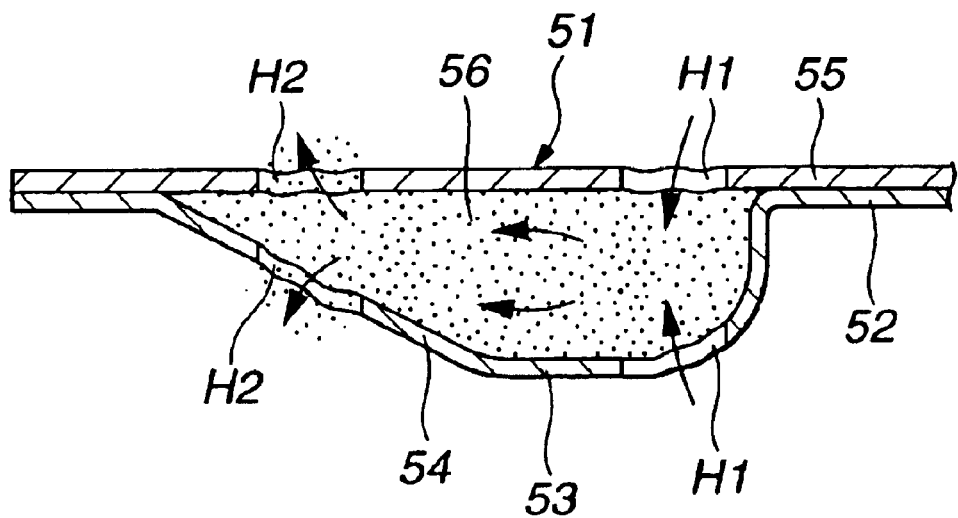
FIG. 30 is a partly enlarged longitudinal cross-sectional view showing air flow and medical powder flow in the medical powder storage chamber of the blister pack (51) of FIG. 28, during initial inhalation action.
Figure 31:
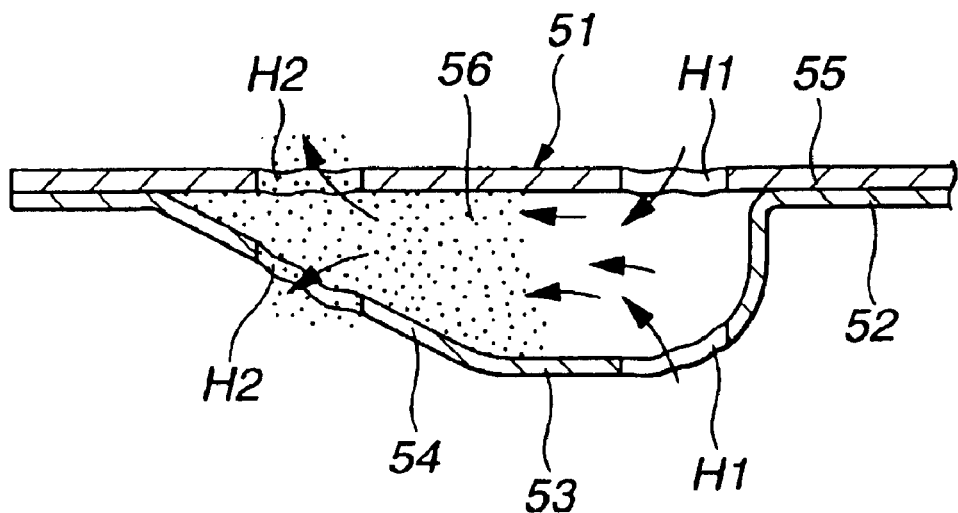
FIG. 31 is a partly enlarged longitudinal cross-sectional view showing air flow and medical powder flow In the medical powder storage chamber of the blister pack (51) in the middle of the inhalation action.

The blister pack 51 shown in FIGS. 28–31 is constructed as previously discussed. Hereinbelow described in detail in reference to FIGS. 30 and 31 are the flow of air passing through the medical powder storage chamber 56 and the flow of medical powder within the storage chamber 56 during inhalation. Inflow holes (H1, H1) and outflow holes (H2, H2) are pricked in the blistered portion 53 of base panel 52 and in the lid panel 54 of blister pack 51 held at the predetermined pricking position, after a series of preliminary setting operations have been completed.

Under these conditions, when a patient draws his or her breath while taking the inhalant port 7 in his or her mouth, at the initial stage of the inhaling action, air introduced through the inflow holes (H1, H1) into the storage chamber 56 is brought into direct-collision with the medical powder pre-stored in the deep recess of blistered portion 53 in which the inflow holes (H1, H1) are pricked. As a result, the medical powder is diffused within the storage chamber 56 at a breath (see FIG. 30). Then, air flow introduced through the inflow holes (H1, H1) acts to gradually flow out the medical powder through the outflow holes (H2, H2) (see FIG. 31).

Figure 32:
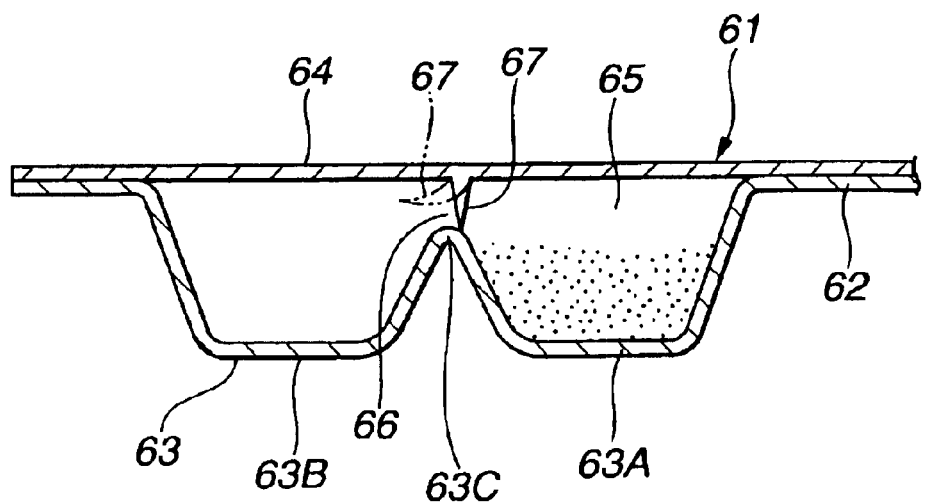
FIG. 32 is a partly enlarged longitudinal cross-sectional view showing another modified blister pack (61), particularly a blistered portion (63), a lid panel (64), a medical powder storage portion (65), a flow-constriction passage (66), and a flap valve (67).

According to the structure of the blister pack 51 having the sloped surface 54 at the outflow side thereof, it is possible to effectively diffuse the medical powder stored in the storage chamber by way of direct collision between the air flow introduced through the inflow holes (H1, H1) into the storage chamber and the medical powder stored. Thus, the blister pack 51 functions to uniformly disperse the medical powder into the entire air flow, while adequately diffusing the medical powder within the storage chamber 56. That is, the blister pack 51 permits medical powder to be stably supplied or inhaled into the lungs of the patient little by little.

Referring now to FIG. 32, there is shown another modified blister pack 61. The modified blister pack 61 is characterized by a flow-constriction orifice passage 66 and a flap valve 67. The flow-constriction passage 66 is located between the radially inward and outward halves of the blistered portion 63 of the blister pack 61. The flap valve 67 is disposed in the flow-constriction passage 66 so that the flap valve fully opens only in presence of a strong inhaling action. The blister pack 61 is comprised of base panel 62, lid panel 64, medical powder storage chamber 65, flow-constriction passage 66, and flap valve 67. The base panel 62 has a thin-walled disc shape and is made of synthetic resin, aluminum material, or the like. As seen in FIG. 32, the base panel 62 has a plurality of blistered portions 63, 63, . . . , 63 (eight blistered portions) around its entire circumference. Each of the blistered portions 63 includes a radially-Inward convex portion 63A and a radially-outward convex portion 63B, and a flow-constriction portion 63C provided between the two convex portions 63A and 63B. The shape and material of the lid panel 64 of blister pack 61 are identical to those of blister pack 21 applied to the inhalant medicator of the second embodiment. The lid panel 64 is formed at its inner wall with the flap valve 67 which opens and closes the flow-constriction passage 66. By hermetically covering the base panel 62 by the lid panel 64, eight medical powder storage chambers 65 are defined between the eight blistered portions 63 of base panel 62 and the lid panel 64. A predetermined amount of medical powder is stored in only the inward convex portion 63A of the two convex portions 63A and 63B of each of the blistered portions, before inhaling action is started. As can be appreciated from comparison between the blister pack 21 applied to the inhalant medicator of the second embodiment shown in FIG. 17 and the blister pack 61 shown in FIG. 32, the blister pack 61 shown in FIG. 32 is different from the blister pack shown in FIG. 17, in that the flow-constriction orifice passage 26 (serving as a fixed orifice) is replaced with the flow-constriction passage 66 and the flap valve 67, and that medical powder is pre-stored in only the upstream side (that is, the inward convex portion 63A) of the two convex portions 63A and 63B. When an inhalation force (or a suction force) of the patient is weak, the flap valve 67 is kept at its closed position indicated by the solid line in FIG. 32, in a manner so as to fully close the flow-constriction passage 66. Conversely, when the patient's inhalation force becomes strong enough to diffuse the medical powder stored in the inward convex portion 63A and to disperse the medical powder into the downstream convex portion 63B, the flap valve 67 is opened to permit fluid-communication between the two convex portions 63A and 63B, as indicated by the two-dotted line in FIG. 32. According to the blister pack 61 having the flap valve 67 disposed in the flow-constriction passage 66, it is possible to inhibit medical powder from being prescribed toward within lungs of the patient in case of a weak inhalation force. In other words, the blister pack 61 is designed to permit medical powder to be prescribed toward within the lungs of the patient, only when a level of the inhalation force exceeds a predetermined threshold value, and thus an acceptable inhalation-force level that adequately diffuses the medical powder is satisfied. Furthermore, it is possible to intermittently or pulsatively prescribe medical powder toward within lungs of a patient by adjusting the magnitude of the inhalation force. As discussed above, the blister pack 61 shown in FIG. 32 insures adequate diffusion of the medical powder, thus enhancing an efficiency of medication.

In the first and second embodiments and all of the modified blister packs (31; 41; 51; 61) shown and described herein, although the inhalant medicator is exemplified in the blister pack having eight blistered portions (or eight medical powder storage chambers), the invention is not limited to the particular embodiments shown and described herein. In lieu thereof, a blister pack having two or more and seven or less blistered portions, or a blister pack having nine or more blistered portions may be used in the inhalant medication. In this case, the number of the recessed fit portions (8A; 80A) of holder (8; 80). the number of the pin insertion hole pairs (8B, 8C), and the number of small recessed fit portions 8D must be set to be identical to the number of the blistered portions.

Figure 33:
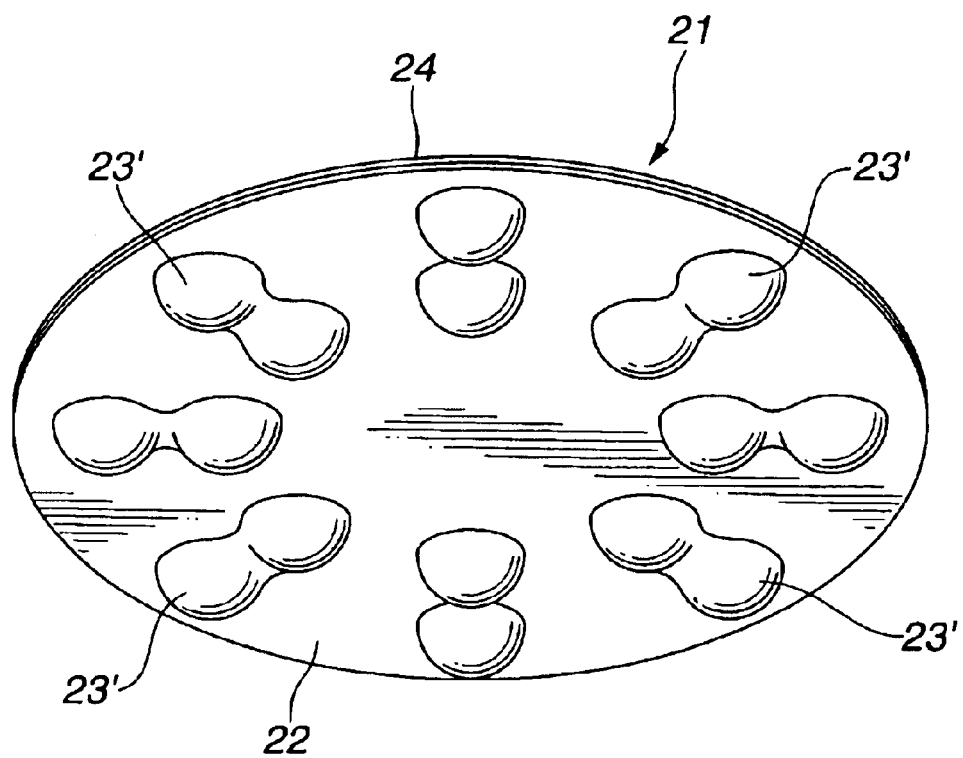
FIG. 33 is a perspective view of a still further modified blister pack with a plurality of guitar-shaped blistered portions (23'), as viewed from its bottom side (its base panel side).

Referring now to FIG. 33, there is shown a modification of the blister pack 21 applied to the inhalant medicator of the second embodiment shown in FIGS. 12–19. In the second embodiment, each of the blistered portions 23 of blister pack 21 is formed as a radially-elongated, elliptical convex portion having the flow-constriction portion narrowed in a direction perpendicular to a flat surface of the lid panel. In lieu thereof, as shown in FIG. 33, a blistered portion may be formed as a radially-extending, guitar-shaped or gourd-shaped convex portion 23' having a narrow part narrowed at its center in a transverse direction. The narrow portion of the gourd-shaped convex portion 23' forms a greatly reduced flow-constriction passage between the two convex portions 23A and 23B, thereby remarkably effectively increasing the flow velocity of air flow through the orifice passage 26.

The entire contents of Japanese Patent Application Nos. P11-352280 (filed Dec. 10, 1999) and P11-352281 (filed Dec. 10, 1999) are incorporated herein by reference.

While the foregoing is a description of the preferred embodiments carried out the invention, it will be understood that the invention is not limited to the particular embodiments shown and described herein, but that various changes and modifications may be made without departing from the scope or spirit of this invention as defined by the following claims.

What is claimed is:

1. A blister pack for an inhalant medicator, comprising:
   a base panel having a blistered portion;
   a lid panel affixed onto an obverse of the base panel to define a medical powder storage chamber by hermetically covering the blistered portion of the base panel;
   the blistered portion comprising:
      (a) a pair of substantially hemispherical convex portions in which inflow and outflow holes are pricked during a preliminary operation of inhalant medication; and
      (b) a flow-constriction portion formed between the substantially hemispherical convex portions to define a flow-constriction orifice passage.

2. The blister pack as claimed in claim 1, wherein the blistered portion is formed as an elliptical convex portion having the flow-constriction portion narrowed in a direction perpendicular to a flat surface of the lid panel.

3. The blister pack as claimed in claim 1, wherein the blistered portion is formed as a gourd-shaped convex portion having a narrow part narrowed at its center in a transverse direction.

4. The blister pack as claimed in claim 1, wherein the inflow and outflow holes are spaced apart from each other by a predetermined distance in a direction substantially parallel to the lid panel of the blister pack.

5. A blister pack for an inhalant medicator, comprising:
   a base panel comprising a blistered portion, the blistered portion comprising:
      (a) a pair of substantially hemispherical convex portion in which inflow and outflow holes are pricked during a preliminary operation of inhalant medication; and
      (b) a flow constriction portion formed between the substantially hemispherical convex portions to define a flow-construction orifice passage;
   a lid panel affixed onto an obverse of the base panel to define a medical powder storage chamber by hermetically covering the blistered portion of the base panel; and
   a flap valve disposed in the flow-constriction orifice passage.

6. A blister pack for an inhalant medicator, comprising:
   a base panel having a blistered portion;
   a lid panel affixed onto an obverse of the base panel to define a medical powder storage chamber by hermetically covering the blistered portion of the base panel;
   the blistered portion comprising:
      (a) a pair of shallow portions in which inflow and outflow holes are pricked during a preliminary operation of inhalant medication; and
      (b) a medical powder collecting portion deeply recessed between the shallow portions to pre-store medical powder therein.

7. The blister pack as claimed in claim 6, wherein the inflow and outflow holes are spaced apart from each other by a predetermined distance in a direction substantially parallel to the lid panel of the blister pack.

8. A blister pack for an inhalant medicator, comprising:
   a base panel having a blistered portion in which inflow and outflow holes are pricked during a preliminary operation of inhalant medication;
   a lid panel affixed onto an obverse of the base panel to define a medical powder storage chamber by hermetically covering the blistered portion of the base panel; and
   the blistered portion comprising:
      an asymmetrical sloped surface which defines a shallow portion at a side of the inflow hole and defines a deep portion at a side of the outflow hole.

9. The blister pack as claimed in claim 8, wherein the inflow and outflow holes are spaced apart from each other by a predetermined distance in a direction substantially parallel to the lid panel of the blister pack.

10. A blister pack for an inhalant medicator, comprising:
   a base panel having a blistered portion in which inflow and outflow holes are pricked during a preliminary operation of inhalant medication;
   a lid panel affixed onto an obverse of the base panel to define a medical powder storage chamber by hermetically covering the blistered portion of the base panel; and
   the blistered portion comprising:
      an asymmetrical sloped surface which defines a shallow portion at a side of the outflow hole and defines a deep portion at a side of the inflow hole.

11. The blister pack as claimed in claim 10, wherein the inflow and outflow holes are spaced apart from each other by a predetermined distance in a direction substantially parallel to the lid panel of the blister pack.

12. A blister pack for an inhalant medicator, comprising:

a base panel having a blistered portion;

a lid panel affixed onto an obverse of the base panel to define a medical powder storage chamber by hermetically covering the blistered portion of the base panel, wherein the lid panel is configured such that inflow and outflow holes are pricked therein and are spaced apart from each other by a predetermined distance during a preliminary operation of inhalant medication;

the blistered portion comprising:
  (a) a pair of substantially hemispherical convex portions in which the inflow and outflow holes are pricked and spaced apart from each other by the predetermined distance during the preliminary operation of inhalant medication; and
  (b) a flow-constriction portion formed between the substantially hemispherical convex portions to define a flow-constriction orifice passage.

13. The blister pack as claimed in claim 12, further comprising:

a flap valve disposed in the flow-constriction orifice passage.

14. The blister pack as claimed in claim 12, wherein the blistered portion is formed as an elliptical convex portion having the flow-constriction portion narrowed in a direction perpendicular to a flat surface of the lid panel.

15. A blister pack for an inhalant medicator, comprising:

a base panel having a blistered portion;

a lid panel affixed onto an obverse of the base panel to define a medical powder storage chamber by hermetically covering the blistered portion of the base panel, wherein the lid panel is configured such that inflow and outflow holes are pricked and spaced apart from each other by a predetermined distance during a preliminary operation of inhalant medication;

the blistered portion comprising:
  (a) a pair of shallow portions in which the inflow and outflow holes are pricked and spaced apart from each other by the predetermined distance during the preliminary operation of inhalant medication; and
  (b) a medical powder collecting portion deeply recessed between the shallow portions to pre-store medical powder therein.

16. A blister pack for an inhalant medicator, comprising:

a base panel having a blistered portion in which inflow and outflow holes are pricked and spaced apart from each other by a predetermined distance during a preliminary operation of inhalant medication;

a lid panel affixed onto an obverse of the base panel to define a medical powder storage chamber by hermetically covering the blistered portion of the base panel, wherein the lid panel is configured such that inflow and outflow holes are pricked and spaced apart from each other by the predetermined distance during the preliminary operation of inhalant medication; and the blistered portion comprising:
  an asymmetrical sloped surface which defines a shallow portion at a side of the inflow hole of the blistered portion and defines a deep portion at a side of the outflow hole of the blistered portion.

17. A blister pack for an inhalant medicator, comprising:

a base panel having a blistered portion in which inflow and outflow holes are pricked and spaced apart from each other by a predetermined distance during a preliminary operation of inhalant medication;

a lid panel affixed onto an obverse of the base panel to define a medical powder storage chamber by hermetically covering the blistered portion of the base panel, wherein the lid panel is configured such that inflow and outflow holes are pricked and spaced apart from each other by the predetermined distance during the preliminary operation of inhalant medication; and the blistered portion comprising:
  an asymmetrical sloped surface which defines a shallow portion at a side of the outflow hole of the blistered portion and defines a deep portion at a side of the inflow hole of the blistered portion.

* * * * *